United States Patent
Zamadar

(10) Patent No.: US 11,324,826 B2
(45) Date of Patent: May 10, 2022

(54) MULTIFUNCTIONAL TREATMENT AND DIAGNOSTIC COMPOSITIONS AND METHODS

(71) Applicant: Matibur Rahaman Zamadar, Nacogdoches, TX (US)

(72) Inventor: Matibur Rahaman Zamadar, Nacogdoches, TX (US)

( * ) Notice: Subject to any disclaimer, the term of this patent is extended or adjusted under 35 U.S.C. 154(b) by 0 days.

(21) Appl. No.: 16/616,437

(22) PCT Filed: Mar. 26, 2018

(86) PCT No.: PCT/US2018/024338
§ 371 (c)(1),
(2) Date: Nov. 22, 2019

(87) PCT Pub. No.: WO2019/190459
PCT Pub. Date: Oct. 3, 2019

(65) Prior Publication Data
US 2020/0121791 A1    Apr. 23, 2020

(51) Int. Cl.
| | | |
|---|---|---|
| A61K 41/00 | (2020.01) | |
| A61K 31/045 | (2006.01) | |
| A61K 33/26 | (2006.01) | |
| A61P 35/00 | (2006.01) | |
| A61K 31/4439 | (2006.01) | |

(52) U.S. Cl.
CPC ........ *A61K 41/0076* (2013.01); *A61K 31/045* (2013.01); *A61K 31/4439* (2013.01); *A61K 33/26* (2013.01); *A61P 35/00* (2018.01)

(58) Field of Classification Search
CPC .... A61K 31/03; A61K 31/045; A61K 31/409; A61K 31/4439; A61K 41/0057; A61K 41/0076; A61K 33/26; C07D 487/22; C07D 403/14; C07F 5/02
See application file for complete search history.

(56) References Cited

U.S. PATENT DOCUMENTS

| | | | |
|---|---|---|---|
| 8,182,785 B2 | 5/2012 | Dussault et al. | |
| 9,155,791 B2 | 10/2015 | Pandey et al. | |
| 9,339,485 B2 | 5/2016 | Geddes | |
| 9,339,557 B2 | 5/2016 | Choi et al. | |
| 9,345,904 B2 | 5/2016 | Tanaka et al. | |
| 9,611,246 B2 | 4/2017 | Bonda et al. | |
| 9,694,075 B2 | 7/2017 | Gerrans et al. | |
| 9,757,357 B2 | 9/2017 | Yuasa et al. | |
| 9,801,922 B2 | 10/2017 | Spitz et al. | |
| 9,839,690 B2 | 12/2017 | You et al. | |
| 9,867,800 B2 | 1/2018 | Bonda et al. | |
| 2003/0082101 A1* | 5/2003 | Taylor | A61K 41/0028 424/1.11 |
| 2009/0005437 A1* | 1/2009 | Gottlieb | A61P 35/02 514/458 |
| 2014/0234238 A1* | 8/2014 | Rudolph | A61K 8/4973 424/59 |

FOREIGN PATENT DOCUMENTS

| | | |
|---|---|---|
| EP | 3210626 | 8/2017 |
| JP | 2009051737 A | 3/2009 |
| WO | 2009/020673 | 2/2009 |

OTHER PUBLICATIONS

M C Berenbaum, et al; title: Meso-Tetra(hydroxyphenyl)porphyrins, a new class of potent tumour photosensitisers with favourable selectivity; British Journal of Cancer; vol. 54, pp. 717-725(1986), Published: Nov. 1, 1986. (Year: 1986).*
Gonçalves PJ, et al; title: Effects of environment on the photophysical characteristics of mesotetrakis methylpyridiniumyl porphyrin (TMPyP); Spectrochimica acta. Part A, Molecular and Biomolecular Spectroscopy, vol. 79, No. 5; pp. 1532-1539, May 17, 2011 (Year: 2011).*
Hou et al, Title: Catalysis of water-soluble porphyrins for oxidation of 1,5-dihydroxy-naphthalene; Gaodeng Xuexiao Huaxue Xuebao (2011), vol. 32(10), pp. 2353-2359, published 2011). (Year: 2011).*
Hou et al, Title: Catalysis of water-soluble porphyrins for oxidation of 1,5-dihydroxy-naphthalene; Gaodeng Xuexiao Huaxue Xuebao (2011), vol. 32(10), pp. 2353-2359, published 2011). English translation. (Year: 2011).*
Authors: Leanne B. Josefsen and Ross W. Boyle; title: Photodynamic Therapy and the Development of Metal-Based Photosensitisers; Met Based Drugs; ID: 276109; published online Sep. 11, 2008. (Year: 2008).*
Silva et a; title: A new non-conjugated naphthalene derivative of meso-tetra-(3-hydroxy)-phenyl-porphyrin as a potential sensitizer for photodynamic therapy; Photochemistry and Photobiology, 2010, 86: 1147-1153, published 2010 (Year: 2010).*
Bizet et al; Photoreduction of Iron(III) Porphyrins; Photochemistry and Photobiology; vol. 34, pp. 315-321; 1981; Pergamon Press Ltd.; UK.

(Continued)

*Primary Examiner* — Anna R Falkowitz
(74) *Attorney, Agent, or Firm* — William R. Childs; Childs Law

(57) ABSTRACT

Multifunctional compositions and methods are provided for therapeutic treatment of bacteria and cancers and for fluorescence diagnosis. Systems generate in situ reactive oxygen species such as singlet oxygen ($^1O_2$), hydroxyl radical (OH) and Juglone, and other chemotherapeutic agents. Methods provided selectively produce greater amounts of one reactive oxygen species over others. Variations are effective in aerobic, anaerobic or $H_2O_2$ rich environments and in presence of, or absence of, light. In $H_2O_2$ rich environment in absence of light, variations decompose $H_2O_2$ into $O_2$ gas to remove excess $H_2O_2$ for elimination of hypoxic environment. Variations are formed of porphyrins, naphthalene derivatives, and metal ions, for illustration, free base tetrakis Ar substituted porphyrine core without metal or halide substitution but having hydroxyphenyl and alkyl pyridyl substituents at meso positions combined with dihydroxynaphthalene and +3 hydrated metal ions.

5 Claims, 19 Drawing Sheets

(56) References Cited

OTHER PUBLICATIONS

Busch et al; Depletion of Tumor Oxygenation during Photodynamic Therapy: Detection by the Hypoxia Marker EF3 [2-(2-Nitroimidazol-1[H]-yl)-N-(3,3,3-trifluoropropyl)acetamide]; Cancer Research 60; 2636-2642; May 15, 2000; Department of Radiation Oncology, University of Pennsylvania, Philadelphia, PA.
Chen et al; Cobalt complexes of BIODIPY as precatalyst for the photooxidation of water than DHN; RSC Adv., 2014, 4, 50693; Royal Society of Chemistry; Sep. 26, 2014; GB.
Chow et al; Amyliodosis presenting as malignant disease; The Lancet Oncology; vol. 5; Aug. 2004; http://oncology.thelancet.com; Elsevier Inc; NL.
Dabrowski et al; Combined effects of singlet oxygen and hydroxyl radical in photodynamic therapy with photostable bacteriochlorins: Evidence from intracellular fluorescence and increased photodynamic efficacy in vitro; Free Radical Biology & Medicine; Jan. 14, 2012; Elsevier; NL.
De Latt et al; Kinetics and Modeling of the Fe(III)/H2O2 System in the Presence of Sulfate in Acidic Aqueous Solutions; Environ. Sci. Technol. 2005, 39, No. 6; 1811-1818; American Chemical Society; US.
Dizdaroglu et al; Damage to the DNA Bases in Mammalian Chromatin by Hydrogen Peroxide in the Presence of Ferric and Cupric Ions; Archives of Biochemistry and Biophysics; vol. 285, No. 2, Mar. 1991; pp. 217-324; The Acedemic Press, Inc.
Dizdaroglu et al; Mechanisms of free radical-induced damage to DNA; Free Radical Research, 46:4, 382-419; DOI: 10.3109/10715762.2011.653969; https://doi.org/10.3109/10715762.2011.653969; Jan. 26, 2012.
Dougherty et al; Photodynamic Therapy; Journal of the National Cancer Institute, vol. 90, No. 12, Jun. 17, 1998.
Fang et al; Juglone exerts antitumor effect in ovarian cancer cells; Iranian Journal of Basic Medical Sciences; 2015; 18:544-548; ijbms.mums.ac.ir.
Felsher Dean W.; Cancer revoked: oncogenes as therapeutic targets; Nature Reviews | Cancer; vol. 3, pp. 375-380; May 2003; Nature Publishing Group.
Folkes, et al; Enhancing the Efficacy of Photodynamic Cancer Therapy by Radicals from Plant Auxin (Indole-3-Acetic Acid); Cancer Research 63, 776-779, Feb. 15, 2003; American Association for Cancer Research.
Foster et al; Oxygen Consumption and diffusion Effects in Phytodynamic Therapy; Radiation Research Society; Radiation Research 126, 296-303 (1991); https://www.jstor.org/stable/3577919.
Fukuzumi, et al; Metal Bacteriochlorins Which Act as Dual Singlet Oxygen and Superoxide Generators; J. Phys. chem B 2008, 112, 2738-2746; American Chemical Society.
Gensch et al; Structural Volume Changes upon Photoexcitation of Porphyrins: Role of the Nitrogen-Water Interactions; J. Am. chem. Soc, 1999; 121, 10573-10582; American Chemical Society.
Hislop et al; The PHotochemical Generation of Hydroxyl Radicals in the UV-vis/Ferrioxalate/H2O2 System; Environ. Sci. Technol. 1999, 33, 3119-3126; American Chemical Society.
Huang et al; A Porphyrin-PED Polymer with Rapid Renal Clearance; Biomaterials, Jan. 2016; 76; 25-32; doi:10.1016/j.biomateirals.2015 10.049.
Isuzugawa et al; Catalase Contents in Cells Determine Sensitivity to the Apoptosis Inducer Gallic Acid; Biol. Pharm. Bull 24(9) 1022-1026; 2001; vol. 24, No. 9; Pharmaceutical Society of Japan.
Ito, Yoshikatsu; Photodegradation of the Cytosine Nucleosides Family by Water-Soluble Iron (III) Porphyrins; Bioconjugate Chem. 1993, 4, 127-133; American Chemical Society.
Kabel, Ahmed M.; Free Radicals and Antioxidants: Role of Enzymes and Nutrition; World Journal of Nutrition and Health; 2014, vol. 2, No. 3; 35-38; Science and Education Publishing.
Kruk et al; Photophysics of the cationic 5,10,15,20-tetrakis (4-N-methylpyridyl) porphyrin bound to DNA, [poly(dA-dT)2, and [poly(dG-dC)]2 interaction with molecular oxygen studied by porphyrin triplet-triplet absorption and singlet oxygen luminescence; Journal of Photochemistry and Photobiology B; Biology 42 (1998) 181-190; Jan. 16, 1998; Elseview; NL.
Kudinova et al; Phytodynamic Therapy of Cancer: Search for Ideal Photosensitizer; Biochemistry (Moscow) Supplement Series B: Biomedical Chemistry; 2010, vol. 4, No. 1, pp. 95-103; Pleiades Publishing, Ltd.
Delatt; A comparative study of the effects of chloride, sulfate and nitrate ions on the rates of decomposition of H2O2 and organic compounds by Fe(II)/H2O2 and Fe(III)/H2O2; Chemosphere 55 (2004), 715-723; Elsevier; NL.
Laine et al; Novel metal-based anticancer drugs: a new challenge in drug delivery; SciVerse ScienceDirect; Current Opinoin in Pharmacology 2012; 12:420-426; Elsevier; NL.
Lennicke et al; Hydrogen peroxide—production, fate and role in redox signaling of tumor cells; Cell Communication and Signaling; (2015) 12:39.
Li et al; Site-Specific Photomodification of DNA by Porphyrin-Oligonucleotide Conjugates Synthesized via a Solid Phase H-Phosphonate Approach; Bioconjugate Chem 1997, 8, 49-56; American Chemical Society.
Lisanti et al; Hydrogen peroxide fuels aging, inflammation, cancer metabolism and metastasis; Cell Cycle 10:15, 2440-2449; Aug. 1, 2011; Landes Bioscience.
Liu et al; Effects and mechanism of juglone in combination with 5-FU on colon cancer CT-236 cells in vivo; BIO Web Conferences 8, 01013 (2017); EDP Sciences.
Lovell et al; Activatable Photosensitizers for Imaging and Therapy; Chem. Rev. 2010, 110; 2839-2857; American Chemical Society.
Luo et al; Principles of Cancer Therapy: Oncogene and Non-oncogene Addiction; Leading Edge Review; 15 pages; Elsevier; NL.
Mao et al; Superoxide Dismutase (SOD)-Catalase Conjugates; The Journal of Biological Chemistry; vol. 268, No. 1, Jan. 5, 1009; pp. 416-420; American Society for Biochemistry and Molecular Biology, Inc.
Nir et al; In vivo effects of porphyrins on bacterial DNA; J. Photochem. Photobiol. B. Biol., 11 (1001) 295-306; Elsevier; NL.
Novak et al; Kenetics of Alachlor Transformation and Identification of metabolites Under Anaerobic Conditions; Pergamon; Wat. Res. vol. 31, No. 12, pp. 3107-3115; 1997; Elsevier; GB.
Ormond et al; Dye Sensitizers for Photodynamic Therapy; Materials 2013, 6, 817-840; doi:10.3390/ma6030817.
Rockley et al; The Photoacoustic Determination of Fluorescence Yields of Dye Solutions; Chemical Physics Letters; vol. 54, No. 3; Mar. 15, 1978; 3 pages.
Rota et al; Evidence for Free Radical Formation During the Oxidation and 2'-7'-Dichlorofluorescin to the Fluorescent Dye 2'-7'-Dichlorofluorescein by Horseradish Peroxidase: Possible Implications for Oxidative Stress Measurements; Free Radical Biology & Medicine; vol. 27, Nos. 7/8; pp. 873-881; 1999; Elsevier; US.
Senge et al; Temoporfin (Foscan, 5,10,15,20-Tetra(m-hydroxyphenyl)chlorin)-A Second-generation Photosensitizer; Photochemistry and Photobiology; 2011; 87; 1240-1296; 57 pages.
Sharman et al; Photodynamic therapeutics: basic principles and clinical applications; Therapeutic focus; DDT vol. 4, No. 11; Nov. 1999; Elsevier Science Ltd; NL.
Standish et al; interstitial Doppler Optical Coherence Tomography as a Local Tumor Necrosis Predictor in Photodynamic Therapy of Prostatic Carcinoma: An In vivo Study; Cancer Res 2008; 68; (23) Dec. 1, 2008; 10 pages; American Association for Cancer Research.
Takizawa et al; Photooxidation of 1,5-dihydroxynaphthalene with iridium compleses as singlet oxygen sensitizers; Photochemical & Photobiological Sciences; 2011, 10, 895; The Royal Society of Chemistry and Owner Societies.
Torti et al; Iron and cancer: more ore to be mined; Nat Rev. Cancer. May 2013; 13(5): 342-355; Macmillan Publishers Limited.
Tromberg et al; In vivo Tumor Oxygen Tension Measurements for the Evaluation of the Efficiency of Photodynamic Therapy; Photochemistry and Photobiology vol. 52, No. 2 pp. 375-385; 1990; Pergamon Press, plc; UK.

(56) References Cited

OTHER PUBLICATIONS

Wang et al; Antibacterial Activity of Juglone against *Staphylococcus aureus*: From Apparent to Proteomic; International Journal of Molecular Sciences; 2016, 17, 965; 12 pages.

Wilkinson et al; quantum Yields for the Photosensitized Formation of the Lowest Electronically Excited Singlet State of Molecular Oxygen in Solution; Journal of Physical and Chemical Reference Data 22, 113 (1993); https://doi.org/10.1063.1.555934; 151 pages; American Institute of Physics for the National Institute of Standards and Technology.

Wilson et al; The Physics, biophysics and technology of photodynamic therapy; Phys. Med. Biol. 53 (2008) R61-109; IOP Publishing; UK.

Wu et al; Broadband Absorbing Polyporphyrin Membrane and Singlet Oxygen Photosensitizer for Photo-oxidation; Macromolecular chemistry and Physics; 215, 280-285; Wiley-Vch Verlag GmbH.

Xia et al; Enhanced Fluorescence emission and Singlet Oxygen Generation of Photosensitizers embedded in Injectable Hydrogels for Imaging-Guided Photodynamic Cancer Therapy; Bio Macromolecules; 2017, 18, 3073-3081; American Chemical Society.

Yan et al; Enhanced Fluorescence Imaging Guided Pyotodynamic Therapy of Sinoporphyrin Sodium Loaded Graphene Oxide; Biomaterials, Feb. 2015; 42; 94-102.

Zhang et al; Anticancer activity and mechanism of juglone on human cervical carcinoma HeLa cells; Can. J. Physiol. Pharmacol. 90: 1553-1558 (2012; NRC Research Press.

United States International Searching Authority; International Search Report & Written Opinion for PCT/US2018/024338; datd Aug. 29, 2018; 10 pages; Alexandria, VA.

Stephenson et al; Mechanistic insights into iron prophyrin-catalyzed olefin epoxidation by hydrogen peroxide: Factors controlling activity and selectivity; Journal of Molecual Catalysis A: Chemical May 22, 2007; vol. 275, p. 54-62.

Xie et al; A SnIV-Porphyrin-Based Metal-Organic Framework for the Selective Photo-Oxygenation of Phenol and Sulfides; Inorganic Chemistry; May 13, 2011; vol. 50, p. 5318-5320.

\* cited by examiner

TMPyP

Fe(III)TMPyP p-THPP m-THPP

FREE BASE TETRAKIS PORPHYRINE CORE, Ar SUBSTITUTENTS (DHN+TMPyP+Fe(III))

Scheme 3(a)

Scheme 3(b)

Scheme 3(c)

$1\times10^{-4}$ M Fe(III)

$1\times10^{-3}$ M Fe(III)

400 μM $H_2O_2$ $1\times10^{-4}$ M Fe(III) and 400 μM $H_2O_2$ $1\times10^{-3}$ M Fe(III) and 400 μM $H_2O_2$

MULTIFUNCTIONAL TREATMENT AND DIAGNOSTIC COMPOSITIONS AND METHODS

GOVERNMENT RIGHTS IN INVENTION

This invention was made with support from Research and Creative Activity grant by Texas' Stephen F. Austin State University Research Enhancement Program (RCA) and Texas Research Grant Funding pursuant to The Welch Foundation (AN-0008 Departmental Grant). While neither support source is directly Federally Sponsored Research or Development, the government may have indirect rights in this invention for research, educational, and clinical purposes.

BACKGROUND OF THE INVENTION

1. Field of the Invention

This invention relates to methods and compositions for therapeutic treatment to slow or stop the progression of bacteria and cancers and for fluorescence diagnosis. In one aspect, this invention relates to multifunctional treatment compositions and methods effective in aerobic, anaerobic or $H_2O_2$ rich environments in presence of, or absence of, light.

In another aspect, this invention relates to in situ generation of one or more reactive oxygen species and a non-toxic chemotherapeutic agent, selected from the group consisting of singlet oxygen ($^1O_2$), hydroxyl radical ($\dot{O}H$), chemotherapeutic agent Juglone, or its derivatives, or combinations thereof, and more specifically to methods to selectively produce a greater amount of one reactive oxygen species over others. In a particular aspect, this invention relates to compositions that, in a $H_2O_2$ rich environment in absence of light in aerobic conditions, produce $\dot{O}H$ and chemotherapeutic agent Juglone or its derivatives and decompose $H_2O_2$ into $O_2$ gas, indicating ability to remove excess toxic $H_2O_2$ and eliminate hypoxic environment by produced $O_2$ gas.

In one specific aspect, this invention relates to multifunctional treatment compositions comprising variations of porphyrin and naphthalene derivatives and certain spatially configured +3 hydrated metal ions, for illustration, compositions comprising a free base tetrakis Ar substituted porphyrine core without metal or halide substitution but having ortho- meta-, or para-hydroxyphenyl and alkyl pyridyl substituents in meso positions and combined with dihydroxynaphthalene and Fe(III) or similar size +3 hydrated metal ions. More particularly, this invention relates to combinations with functionality of results of combination of cationic (i) meso-tetra(N-methyl-4-pyridyl)porphine tetrachloride (TMPyP) or (ii) meso-tetra(x-hydroxyphenyl)porphine where x is o-, m-, or p-, with 1,5-dihydroxynaphthalene (DHN) and Fe(III) ions in aqueous solution and the reaction products thereof.

2. Description of the Related Art

Prior art traditional cancer treatments such as surgery, radiation, and traditional chemotherapy have limitations. In general, such treatments lack selectivity for removing or killing malignant tumor tissues and are costly or highly invasive or administer toxic treatments. Prior art includes metal-based drugs for cancer treatment, for example cisplatin has long been used. However such metal-based drugs are reported to lack selectivity and have poor water solubility, pharmacological deficiencies, and serious side effects such as kidney and nerve damage, hearing loss, vomiting and others. Thus, there is a continuing need for better therapeutics which can selectively react with chemical components already present in cancer cells and produce reactive species capable of killing those cancer cells.

In addition, prior art treatments are not easily synthesized or readily available to the poor in developing or developed countries. Studies project world-wide cancer-related deaths will increase seventy percent (70%) by 2040.

Thus, there is a need for improved, non-toxic, noninvasive, low cost effective cancer therapy methods enabled by compositions that can be readily prepared without specialized costly synthesis equipment or extensive training.

Prior art photodynamic therapy (PDT) methods for cancer treatment are an alternative to the traditional methods but also have limitations. PDT involves homing to or localization of photosensitizers in target tissue at or near tumors, for example, skin, prostate, and lung cancers. Upon illumination with visible light or other irradiation with excitation light, photosensitizers transfer energy to ground or lower state oxygen and generate highly reactive singlet oxygen ($^1O_2$), as a critical intermediate by reacting with cells of targeted adjacent tissues and result in death of cancer cells. Compared to traditional non-PDT treatments, prior art PDT treatments are relatively low cost, better tolerated as diseased tissues are treated non-invasively, and are of low toxicity with low mutagenic potential. Some prior art PDT treatments provide results from single treatment, and others allow possibility of repeat treatments at the same target site without a total-dose limitation.

However, tumor hypoxia at a target tumor cell site is a significant problem for prior art PDT compositions and methods. Tumor hypoxia limits prior art clinical utility because PDT photochemistry highly depends on the presence of oxygen ($O_2$) for producing cancer lethal singlet oxygen ($^1O_2$).

Since every photosensitization reaction uses light to sensitize dissolved oxygen ($O_2$) to singlet oxygen ($^1O_2$), PDT methods are completely ineffective in the absence of light.

PDT is also currently significantly limited by the insufficient generation of singlet oxygen. Insufficient generation of singlet oxygen, at least in part, at the target site is due to (i) insufficient photosensitizers localized at the target site, (ii) not enough visible light at the target site, and (iii) photosensitizer not having favorable or suitable triplet excited states.

There is a need for improved singlet ($^1O_2$) generation from photosensitizers by dissolving or contacting more photosensitizers in tissue media and allowing a suitable low-lying triplet state porphyrin sufficient time for ground-state oxygen in the relatively unreactive triplet state ($^3O_2$) to transform to an excited state forming reactive singlet oxygen ($^1O_2$). After much prior art work, issues remain for finding a suitable low-lying triplet porphyrin for efficient singlet oxygen formation with desired phosphorescence emissions (triplet quantum yield of energy at least 94 KJ/mol).

Other significant existing problems with prior art PDT treatments limit their singlet oxygen reactive oxygen species and effectiveness to narrow ranges. These other limitations include (1) poor solubility of hydrophobic photosensitizers in bodily tissue or injectable solvent, for illustration, hydrophobic porphyrins may form aggregates in aqueous environment leading to insufficient tumor localization; (2) limited penetration of light into fatty and deeper tissues; (3) preparation involves complex organic/inorganic synthesis and difficult purification procedures for obtaining chemically pure PDT effective compounds; (4) need for lower toxicity and rapid clearance from the body; and (5) lack of dual or multiple functionality to address changes in conditions at site of application.

A need continues for suitable compositions and methods to treat cancers that possess dual or multiple functionality. For illustration, the prior art reports zinc bacteriochlorin is an effective dual photosensitizer capable of producing two reactive oxygen species such as singlet oxygen and superoxide in an aprotic solvent. However, the use of these dual photosensitizers was found to be ineffective in the absence of dissolved oxygen and light and are ineffective in an aqueous environment.

Well known in the prior art of tumor biology is that malignant cells produce more hydrogen peroxide than normal healthy cells. However, there is a lingering need for improved compositions and therapeutic methods to decompose excess hydrogen peroxide $H_2O_2$ into hydroxyl radical (ȮH) capable of damaging lipids, proteins, and DNA leading to an ultimate cancer cell death.

Prior art publications indicate a therapeutic method using the Fenton reaction for $H_2O_2$ decomposition by Fe(II) ions into hydroxyl radical (ȮH). However, prior art synthesis of iron-based therapeutics for use in Fenton reaction is expensive and time-consuming and involves complex purification procedures. In addition, such require special training and expertise in organic and inorganic synthesis. Moreover, in some instances, resulting compositions do not pass toxicity tests due to the inherent toxic nature of the associated ligands. Furthermore, Fenton reactions from prior art iron-based therapeutics form iron-containing sludge ($Fe(OH)_3$) during the course of reaction, which reduce capability for hydroxyl radical production.

Thus, there is continuing need for a non-toxic treatment system, without sludge formation, that is capable of generating reactive oxygen species under various reaction conditions in aqueous solution, which is multifunctional by being active in $H_2O_2$ rich environments, can be used in aerobic and anaerobic aqueous environments, effective in presence or absence of light, and able to produce non-toxic chemotherapeutic drugs in situ.

Therefore, the long felt need continues for a low cost chemotherapeutic drug solution, available for both developing and developed countries, which can easily be prepared from commercially available chemicals with highest grade of purity, and where little or no special equipment, skills or specialized training are required.

SUMMARY OF THE INVENTION

I have discovered a treatment and diagnostic system by combining features of photodynamic therapy with other anticancer therapeutic methods. This discovery comprises multifunctional treatment and diagnosis systems which comprise at least one reactive oxygen species produced in situ and at least one non-toxic chemotherapeutic agent. Said system slows or stops the progression of bacteria or cancer thus treating various malignancies and bacterial infections. I have found also that variations of said system are fluorophores and function for photodynamic diagnosis.

Variations of these compositions and methods are multifunctional, being capable of producing in situ one or more reactive oxygen species and chemotherapeutic agents under various reactions conditions, such as in aerobic, anaerobic or $H_2O_2$ rich environments in presence of, or absence of light, being production capable within any of such conditions at the same time or any time or in rapid condition switch sequence from one condition to the other, for illustration, light to dark or aerobic to anaerobic. Variations are further multifunctional in being therapeutic and diagnostic.

In particular variations, I have discovered compositions and methods that produce one or more reactive oxygen species and Juglone based chemotherapeutics in situ. I have found methods for producing hydroxyl radicals in situ in all of (i) aerobic conditions (ii) in anaerobic conditions and (iii) in $H_2O_2$ rich environments. I also found methods for producing Juglone based chemotherapeutics in situ in all of (i) aerobic conditions (ii) in anaerobic conditions and (iii) in $H_2O_2$ rich environments. I further found methods for generating singlet oxygen (i) in aerobic conditions and (ii) in anaerobic and aerobic $H_2O_2$ rich environments.

As used in the Specification and Claims,

"DHN" means one or more isomers of dihydroxynaphthalene including the 1,5-form shown in FIG. 1A, 1,5-dihydroxynaphthalene as well as isomers such as 1,x-dihydroxynaphthalene, where x is 2, 3, 4, or 8 or isomers such as 2, x-dihydroxynaphthalene, where x is 3 or 6. Single 'hydroxy' naphthalene reacts similarly to DHN under certain conditions in presence of porphine and metal ions for treatment or diagnostic combinations of this invention, and when so reacting, it is considered a reaction analog within term "DHN";

"Juglone" means 5-hydroxy-1,4-naphthalenedione form as shown in FIG. 1B, but also includes other isomers;

"Derivatives of Juglone" means reaction intermediates or products involving Juglone in reaction path;

"TMPyP" means commercially available free base meso-tetra(N-methyl-4-pyridyl) porphine tetrachloride as shown in FIG. 4A;

"Fe(III)TMPyP" means commercially available Fe(III) bound meso-tetrakis(N-methyl-4-pyridyl) porphyrin as shown in FIG. 4B;

"m-THPP" means commercially available meso-tetra(m-hydroxyphenyl)porphine, also (5,10,15,20-tetrakis(3-hydroxyphenyl)-21H,23H-porphine) in FIG. 4C;

"p-THPP" means commercially available meso-tetra(p-hydroxyphenyl)porphine, also (5,10,15,20-tetrakis(4-hydroxyphenyl)-21H,23H-porphine) in FIG. 4D;

"o-THPP" means meso-tetra(o-hydroxyphenyl)porphine, also (5,10,15,20-tetrakis(2-hydroxyphenyl)-21H,23H-porphine), not shown;

"ArPP" or "free base tetrakis porphyrine core without metal or halide substitution" means as shown in FIG. 5A wherein each of the four Ar substituents are at meso positions and are the same, and "Ar substituents" means also as shown in FIG. 5A wherein ArPP comprises for example, one or more of TMPyP, o-THPP, m-THPP, and p-THPP;

"(DHN+TMPyP+Fe(III))" means one embodiment of a claimed treatment composition of this invention as shown in FIG. 5B;

"hMe(III)" or "hMe(III)+" or "hydrated metal having a +3 ionic state with spatial attributes at molecular level at or near that occupied by Fe(III)" means hydrated metals in +3 state which have comparable size or spatial geometry under reaction conditions near that of Fe(III)+, where hME(III) is understood to have a positive charge, for illustration, "Fe (III)", such as that from Iron halides and further means anhydrous Fe halides which are subsequently hydrated and among others, such as tetraaquadichloroiron(III) chloride dihydrate and hexahydrate $FeCl_3 \lfloor 6H_2O$;

"(ArPP, DHN, and hMe(III))" or "(ArPP+DHN+hMe (III))" means free base tetrakis Ar substituted porphyrine core without metal or halide substitution wherein each of the four Ar substituents are the same and Ar are selected from the group consisting of any of ortho- meta-, or para-hydroxyphenyl and alkyl pyridyl as shown in FIG. 5A dihydroxynaphthalene as shown in FIG. 1A or hydroxynaphthalene, and hydrated metal having a +3 ionic state with spatial attributes at molecular level at or near that occupied by Fe(III);

"Treatment composition" means one or more variations of (ArPP+DHN+hMe(III)) and reaction product or other result of combination of ArPP, DHN, and hMe(III);

"Singlet oxygen" means "($^1O_2$)";

"Hydroxyl radical" means "(ȮH)";

"$H_2O_2$" means hydrogen peroxide, particularly in context of presence at, near or within a malignant cell;

"ROS" means reactive oxygen species comprising singlet oxygen, hydroxyl radical, or other chemotherapeutic species comprising oxygen;

"SOSG" means singlet oxygen sensor green detector;

"PDT" means photodynamic therapy;

"$H_2O_2$ rich environment" means at, near or above safe dose of 200 to 400 micro-molar (μM) in context of $H_2O_2$ at location of tumor, where increased amount may cause cell damage;

"Non-toxic chemotherapeutic agent" of this invention means one or more reaction or resultant products of treatment composition (ArPP, DHN, and hMe(III)) comprising one or more of ROS, Juglone or derivatives of Juglone;

"Fenton-like reaction" of this invention means as shown in FIG. 6A Scheme 3(a); and "in situ", in context of combination of variations of ArPP with DHN and hMe(III)), means examining the reaction products, mixtures or other combination results, regardless of where or order combination or result occurs, for illustration, not limitation in a test tube or contact with mammalian tissue or fluid, examining result exactly in place where result occurs.

I have found compositions and methods of generating in situ one or more reactive oxygen species, including without limitation, singlet oxygen ($^1O_2$), hydroxyl radical (ȮH), chemotherapeutic agent, Juglone, or its derivatives or combinations thereof, by use in aerobic, anaerobic or $H_2O_2$ rich environment in presence of, or absence of light. These claimed compositions and methods are multifunctional, as further described herein.

Under visible light irradiation, treatment compositions of this invention produce $^1O_2$, ȮH, and Juglone or derivatives of Juglone in aerobic conditions.

And surprisingly, the same treatment compositions also produce ȮH and Juglone or derivatives of Juglone, or combinations thereof, in the presence of visible light in anaerobic conditions.

Most surprisingly, in a $H_2O_2$ rich environment, treatment compositions of this invention effectively produce ȮH and Juglone or derivatives of Juglone by reacting with $H_2O_2$ via Fenton-like reaction in absence of light in aerobic conditions. In addition to ȮH's formation from $H_2O_2$, the composition decomposes $H_2O_2$ into $O_2$ gas providing an ability to remove excess toxic $H_2O_2$ as well as ability to eliminate hypoxic environment by produced $O_2$ gas.

I have unexpectedly found a method to adapt and use the treatment compositions to selectively produce one reactive oxygen species over others by varying concentration of hMe(III) ions in the treatment composition. The treatment compositions are highly soluble in an aqueous environment due to their ionic nature and do not form any aggregates at preferred concentrations in aqueous environments.

Also, I found the treatment compositions fluoresce in aqueous solution to a reasonable extent so that they can be used for photodynamic diagnosis. In addition, I found the treatment composition possesses great antibacterial properties, particularly against *E. coli* bacteria in aerobic and in $H_2O_2$ rich environments, in presence of or absence of light.

Thus, the compositions of this invention have characteristics which slow or stop the progression of bacteria and other cells such as cancers. Treatment can be by a single dose of composition and in other variations, repeated doses are tolerated.

One embodiment of multifunctional compositions of this invention comprises variations of hMe(n), porphyrin and naphthalene derivatives. In a specific preferred embodiment, compositions for treatment and diagnosis are formed from various amounts of cationic meso-tetra(N-methyl-4-pyridyl) porphine tetrachloride (TMPyP), Fe(III) ions, and 1,5-dihydroxynaphthalene (DHN), preferably in aqueous solution. I found that such embodiments of treatment compositions of this invention produce in situ $^1O_2$, ȮH, and Juglone or derivatives of Juglone (non-toxic chemotherapeutic drugs) under visible light irradiation in aerobic aqueous solution; however, I also found that the same treatment compositions produce ȮH, and Juglone or derivative of Juglone in anaerobic aqueous solution under visible light irradiation. Furthermore, I found that said treatment compositions produce $O_2$ from excess $H_2O_2$ in dark and were capable of eliminating excess $H_2O_2$. Quite remarkably, I found that they also generated ȮH, and Juglone or one or more derivatives of Juglone from a Fenton-like reaction in dark. An investigation of fluorescence properties of these embodiments of treatment compositions revealed that these variations fluoresce in aqueous medium lending ability to be used for image guided PDT diagnostics application. Finally, this embodiment of treatment composition shows a great antibacterial property, particularly against *E. coli* bacteria, and tunable properties were achieved by varying the concentration of the components of the treatment composition.

It is important that I have discovered treatment compositions that can easily be prepared from commercially available chemicals, and without special equipment, skills or training required, allowing potential for them to be readily available at lower cost in developing and developed countries.

As used in this Specification and the Claims, the term "treatment" includes therapeutic effects by action of one or more agents toward remedial, beneficial, corrective, restorative, or healing results, and the term "diagnosis" means fluoresces in aqueous medium having ability to be used for image guided photodynamic diagnostic applications, and the term "fluorescence diagnosis" as part of "diagnosis" means generation of one or more optical results from a biological fluid or tissue of interest by reaction or other interaction with a composition of this invention, wherein such composition emits electromagnetic energy such as light at a certain wavelength when the composition or result of application of the composition to home to such fluid or tissue and such are illuminated by radiation of a selected wavelength. The term "multifunctional" when used with composition or method of this invention means the composition or method may have one or more features selected from the group consisting of the following: (a) in presence of or absence of light, it produces in situ one or more reactive oxygen species such as, singlet oxygen ($^1O_2$), hydroxyl radical (ȮH), chemotherapeutic agent, Juglone, or its derivatives in aerobic, anaerobic or $H_2O_2$ rich environment; (b) in the presence of visible light irradiation, it produces $^1O_2$, ȮH, and Juglone or derivatives of Juglone in aerobic conditions and produces ȮH and Juglone or derivatives of Juglone in anaerobic conditions; (c) in absence of visible light in aerobic conditions, it produces ȮH and Juglone or derivatives of Juglone by reacting with $H_2O_2$ via a Fenton-like reaction, and when reacted with $H_2O_2$, the treatment composition converts $H_2O_2$ to $O_2$ gas and water, evidencing potential to remove not only toxic $H_2O_2$ but also to eliminate hypoxic conditions by producing $O_2$ gas; (d) it fluoresces in aqueous solution and shows potential for photodynamic diagnosis applications; (e) it has antibacterial properties, shown for illustration, by inhibiting the growth of *E. coli* in aerobic and $H_2O_2$ rich environment in both the presence and absence of light, or (f) treatment or diagnosis is effective by a single dose or repeated doses are tolerated.

Other features and advantages of the invention will be apparent from the following detailed description, examples, drawings and claims.

BRIEF DESCRIPTION OF THE DRAWINGS

FIG. 5 is theoretical architecture for structural drawing of one embodiment of claimed treatment compositions, wherein in FIG. 5A shows an embodiment of claimed free base tetrakis Ar substituted porphyrine core without metal or halide substitution, with claimed Ar substituents and wherein

DETAILED DESCRIPTION OF THE INVENTION

Figure 1A:
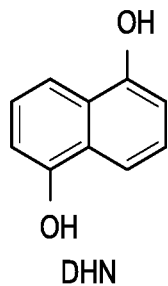
FIG. 1 is chemical structure drawing of commercially available DHN at FIG. 1A DHN and Juglone at FIG. 1B.
Figure 1B:
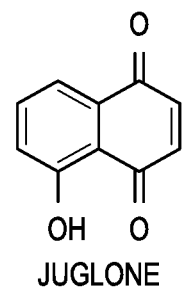

I have discovered, as one embodiment of this invention, a composition comprising (a) a combination of (1) free base tetrakis Ar substituted porphyrine core without metal or halide substitution wherein each of the four Ar substituents are at meso positions, are the same, and Ar are selected from the group consisting of any of ortho- meta-, or para-hydroxyphenyl and alkyl pyridyl, (2) dihydroxynaphthalene or hydroxynaphthalene and (3) hydrated metal having a +3 ionic state with spatial attributes at the molecular level at or near that occupied by Fe(III) and (b) one or more resultant effects of combinations of above said (a)(1) porphyrine core, said (a)(2) substituted or unsubstituted hydroxynaphthalene and said (a)(3) hydrated +3 metal. The term "resultant effect" is used in the Specification and Claims to mean any of (i) a reaction product or (ii) coordination entity or complex formed by association of molecular entities from components of said combined (a)(1) porphyrine core, (a)(2) naphthalene based component and (a)(3) hydrated +3 metal of said composition, either alone or with components present in mammalian tissue or fluid. Thus, one variation of resultant effect may be a molecular entity resulting from loose association involving two or more component molecular entities from combination of (a)(1) porphyrine core, (a)(2) naphthalene based component and (a)(3) hydrated +3 metal of said composition, either alone or with components present in mammalian tissue or fluid.

In one variation, said (b) resultant effect is one or more chemotherapeutic therapies selected from a group consisting of singlet oxygen, hydroxyl radical, and Juglone or its derivatives. Thus, said compositions can be effective for either treatment or diagnosis of malignancy, bacterial infection, Alzheimer's symptoms and other conditions, or for both treatment and diagnosis at the same time depending on conditions of use.

In an embodiment of this invention important to production of targeted results, I have discovered that if the amount of (a)(3) hydrated metal is increased or decreased in relation to combined amounts of said (a)(1) porphyrine or said (a)(2) naphthalene based material, then relative amounts of components produced as resultant effects, such as singlet oxygen, hydroxyl radical, and Juglone or its derivatives, can be changed in a manner whereby one or more preferred resultant effect, for example singlet oxygen over hydroxyl radical or Juglone, is increased or decreased in proportion to one or more other resultant effects.

I have discovered that, by changing the amount of hydrated metal present relative to porphyrine or naphthalene based material, the relative reactivity or coordination ability of one or more other components of the combination can be changed, for illustration, in the instance of achieving a desired rate of photooxidation of dihyroxynaphthalene by meso-tetra(N-methyl-4-pyridyl)porphine tetrachloride, and it is uncertain whether such change I found is by impact on coordination stability, reactivity, stereochemistry or other characteristic of the combination. For illustration, not limitation, in one variation of composition of invention, resultant effect (b) comprises singlet oxygen, hydroxyl radical, and Juglone or its derivatives and the ratio of mole of (a)(3) hydrated metal present is increased or decreased in relation to moles present of porphyrine and naphthalene based material to increase or decrease presence of one or more desired resultant effect of selected from singlet oxygen, hydroxyl radical, and Juglone or its derivatives, in relation to others.

I have also found embodiments of this invention that have multifunctional activity for treatment or diagnosis in absence of or presence of light and in either, or both, aerobic and anaerobic conditions. I have also found multifunctionality can be determined by changing ratios of combinations of (a)(1) porphyrine, (a)(2) naphthalene based material and (a)(3) hydrated +3 metal. For illustration, not limitation, multifunctional compositions can be made by combining (a)(1) porphyrins selected from one or more of the group consisting of meso-tetrakis(N-methyl-4-pyridyl) porphine tetrachloride, meso-tetrakis(o-hydroxyphenyl)porphine, meso-tetrakis(m-hydroxyphenyl)porphine, and meso-tetrakis(p-hydroxyphenyl)porphine and (a)(2) of dihydroxynaphthalene and (a)(3) of hydrated Fe(III) chloride with (b) resultant effect comprising hydroxyl radical. The resultant effect with hydroxyl radical so produced has multifunctional activity for treatment, being effective in absence of or presence of light and in either, or both, aerobic and anaerobic conditions.

In one variation of this embodiment of this invention, a composition is provided comprising an aqueous solution of porphyrine selected from one or more of the group consisting of meso-tetrakis(N-methyl-4-pyridyl) porphine tetrachloride, meso-tetrakis(o-hydroxyphenyl)porphine, meso-tetrakis(m-hydroxyphenyl)porphine, and meso-tetrakis(p-hydroxyphenyl)porphine with dihydroxynaphthalene and Fe(III) chloride and resultant effect comprises one or more of hydroxyl radical, singlet oxygen, and Juglone or its derivatives. With such variation, the mole ratio of Fe(III) chloride is increased or decreased in relation to moles of said porphyrines and dihydroxynaphthalene to change of resultant effect ratios produced of said singlet oxygen, hydroxyl radical, and Juglone or its derivatives.

In a specific variation of an embodiment of a composition of this invention, TMPyP is combined with 1,5-DHN and hydrated Fe(III) in mole ratios of (i) TMPyP to 1,5-DHN of 1 to 18 to 22, (ii) TMPyP to Fe(III) ions of 1 to 15 to 18.33 and (iii) 1,5-DHN to Fe(III) of 1.1 to 1.3, wherein final concentration of hydrated Fe(III) is adjusted and selected to achieve desired rate of photooxidation of DHN by TMPyP More preferably, the initial mole ratios of TMPyP to DHN to Fe(III) are of 1 to 20 to 16.67, then final concentration of hydrated Fe(III) is adjusted and selected to achieve a maximum rate of photooxidation of DHN by TMPyP.

In one embodiment of this invention, a multifunctional treatment system comprising 1,5-dihydroxynaphthalene, meso-tetra(N-methyl-4-pyridyl)porphine tetrachloride and Fe(III) chloride in aqueous solution is provided. Such system is multifunctional by producing in situ at least one non-toxic chemotherapeutic agent from a single dose in presence of visible light or in absence of light, effective as treatment composition in both aerobic and anaerobic environments as well as in $H_2O_2$ rich environment, enabling production of $O_2$ from excess $H_2O_2$ when $H_2O_2$ is present and produces both (a) singlet oxygen and hydroxyl radicals in aerobic conditions and (b) hydroxyl radicals in anaerobic conditions. One preferred variation of this embodiment is a combination comprising TMPyP, DHN and Fe(III) ions at mole ratios of 1 TMPyP to 20 DHN to 16.67 for initial Fe(III), wherein is combined as TMPyP as $1.8 \times 10^{-8}$ moles of TMPyP obtained from (3 mL of $6.0 \times 10^{-8}$ M), equivalent of $1.47 \times 10^{-5}$ g (Mwt for TMPyP-818.20), 1,5-DHN is combined to be present in amount of $3.6 \times 10^{-7}$ moles obtained from (36 μL of $1.0 \times 10^{-2}$ M), equivalent to $5.67 \times 10^{-5}$ g (Mwt for DHN-160.05) and hydrated Fe(III) ions in combined at an initial amount of $3.0 \times 10^{-7}$ moles obtained from (30 μL of $1.0 \times 10^{-2}$ M), equivalent to $4.82 \times 10^{-5}$ g (Mwt for $FeCl_3$-160.84) but Fe(III) is adjusted to an amount within the range of 15 μL of $1.0 \times 10^{-2}$ M to 50 μL of $1.0 \times 10^{-2}$ M to adjust rate of photooxidation of DHN by TMPyP to produce greater quantities of one or more preferred chemotherapeutic result effects selected from the group consisting singlet oxygen, hydroxyl radical, and Juglone or its derivatives.

In a first process embodiment of this invention, a method to produce one or more reactive oxygen species and Juglone or its derivatives in situ is provided as resultant effect of combining ArPP, DHN, and hMe(III)+. In one variation, optionally the mole ratio of hMe(III)+ is increased or decreased in relation to mole ratios of ArPP and DHN to selectively produce greater or lesser amount of one reactive oxygen species or Juglone or its derivatives over other resultant effects. Specific enablement of methods of preparation of solutions of components of treatment compositions are taught by the Examples below.

In another embodiment, a method to produce hydroxyl radicals in situ in presence of light or absence of light, wherein in absence of light and in anaerobic conditions, hydroxyl radical (ȮH) is produced upon reacting with hydrogen peroxide ($H_2O_2$), is provided as a resultant effect of combining ArPP, DHN, and hMe(III)+. In a variation, a method to produce hydroxyl radicals in situ in a condition which is aerobic, anaerobic, or $H_2O_2$ rich environment or any sequence or combination of said conditions, is provided by combining ArPP, DHN, and hMe(III)+ in presence or absence of light wherein in absence of light and in anaerobic conditions, hydroxyl radical (ȮH) is produced upon reacting combination of ArPP, DHN, and hMe(III)+ with hydrogen peroxide ($H_2O_2$).

When a Juglone family member is desired as treatment, one embodiment of a method of this invention combines ArPP, DHN, and hMe(III)+ in presence or absence of light to produce Juglone or Juglone derived chemotherapeutics in situ in a condition which is aerobic, anaerobic, or $H_2O_2$ rich environment or any sequence or combination of said conditions.

When singlet oxygen is desired as treatment, another method of this invention produces singlet oxygen in situ in presence of light in a condition which is which is aerobic, anaerobic, or $H_2O_2$ rich environment or any sequence or combination of said conditions by combining ArPP, DHN, and hMe(III)+ in presence of light.

When one or more of singlet oxygen ($^1O_2$), hydroxyl radical (ȮH), Juglone or Juglone derivatives are desired as a treatment in presence of visible light and in aerobic condition, yet another method of this invention produces those treatments in presence of visible light and in aerobic condition by combining ArPP, DHN, and hMe(III)+ in light and aerobic conditions.

When one or more of hydroxyl radical (ȮH) derived from hydrogen peroxide ($H_2O_2$), Juglone or Juglone derivatives are desired as a treatment in absence of light and in anaerobic condition, ArPP, DHN, and hMe(III)+ are combined in absence of light and in anaerobic condition to produce such desired treatments.

In an especially important multifunctional embodiment of this invention, for transition to and from "light and dark" conditions and for changing "aerobic and anaerobic conditions" during treatment stages, a method of producing one or more non-toxic chemotherapeutic treatments is provided for such transition and change of conditions by combining ArPP, DHN, and hMe(III)+ and forming at or near mammalian tissue or fluid in one or more regions of treatment (a) in presence of visible light (1) in an aerobic condition, one or more of singlet oxygen ($^1O_2$), hydroxyl radical (ȮH), and one or more of Juglone or Juglone derivatives, then concurrently or sequentially (2) in an anaerobic condition, hydroxyl radical (ȮH) and Juglone or Juglone derivatives, then forming either concurrently or subsequently forming at or near mammalian tissue or fluid in one or more different regions of treatment (b) in absence of light, hydroxyl radical (ȮH) upon reacting ArPP, DHN, and hMe(III)+ with hydrogen peroxide ($H_2O_2$) and one or more of Juglone or Juglone derivatives. In preferred variation of such method for changing conditions, use of multifunctional treatment system comprising 1,5-dihydroxynaphthalene, meso-tetra(N-methyl-4-pyridyl)porphine tetrachloride and Fe(III) chloride in aqueous solution is preferred.

In one embodiment, this invention provides a method to treat tumor hypoxia by oxygenating a less well-oxygenated necrotic region of a solid mammalian tumor having a wide range of oxygen concentrations not just at extremes of fully oxygenated or fully hypoxic, by combining ArPP, DHN, and hMe(III)+ and adjusting concentration of hMe(III)+ ions combined with DHN and ArPP to enable control of the rate of oxidation of DHN by ArPP in the presence of selected amounts of hMe(III)+ ions to form a tailored treatment composition as non-toxic chemotherapeutic agent of choice by selectively activating one or more of resulting reaction products of singlet oxygen ($^1O_2$), hydroxyl radical (ȮH), Juglone, or its derivatives as nontoxic reaction product or product of choice in in lieu of one or more of other reaction products. Such selective activation can be obtained alternatively by applying with other variations, according to herein described teachings for changes of conditions. In preferred variation of such method for treating tumor hypoxia, use of multifunctional treatment system comprising 1,5-dihydroxynaphthalene, meso-tetra(N-methyl-4-pyridyl)porphine tetrachloride and Fe(III) chloride in aqueous solution is preferred.

Unlike most prior art chemotherapy, I have found that the above described and claimed combinations and methods of this invention can be effective in a relatively short period of time, and in a non-toxic manner. I have found that combinations and methods of this invention for preparation of treatment and for its dispensing for application require less than one (1) hour. Such preparation, dispensing and application can be substantial completed, as demonstrated by Examples below, in less than twenty (20) to thirty (30) minutes, and in certain instances about fifteen (15) minutes. Such short application time enables rapid, effective field treatments, and may include certain diagnosis, in locations at which any kind of treatments or diagnosis were heretofore prohibited.

Thus, one additional significant advantage over prior art treatments of the various compositions and methods of this invention is enablement of portable treatment and diagnosis, under differing field conditions with kits being prepared from commercially available materials, which kits can be easily stored, readily transported without activation, and then activated as needed at a remote site of treatment, such as remote regions of a developed country or of a developing countries. Treatments including diagnosis herein claimed being enabled on site without specialized synthesis apparatus or training.

In one embodiment of this invention, a portable field treatment kit for preparation of treatment composition mixture for remote locations such as those distanced away from synthesis laboratories or typical chemotherapy centers, or when other rapid preparation and administration are preferred for reasons other than location, is provided and comprises (a) a visible light resistant durable but flexible package with one or more exterior layers, (b) at least three (3) separate sealed, compartments within said exterior layer, with one (1) compartment of premeasured quantities of each component ArPP, DHN, and hMe(III)+ and optionally a fourth (4) compartment for excipient for injection or topical use, all within a single package or assembled separately as a collection of packages, each compartment being breakable upon application of pressure to exterior layers enable combining ArPP, DHN, and hMe(III)+, with optional excipient in any, to form treatment composition with optional excipient and (c) syringe and needle or other extracting and administering means to extract and inject or extract and topically dispense the treatment composition with optional excipient. Falling within the foregoing is use a simple field knife or other cutter means to extract and then topically dispense the treatment composition. In preferred variation of such kit for portable treatment, use of multifunctional treatment system comprising 1,5-dihydroxynaphthalene, meso-tetra(N-methyl-4-pyridyl)porphine tetrachloride and Fe(III) chloride in aqueous solution is preferred. Falling within the foregoing treatment is basic field diagnosis by use of suitable portable optic fluorescence sensor.

The treatment compositions of the present invention are thus useful in general, in the manner known in the art for treatment of bacteria or of cancers or for fluorescence diagnosis. For use in in vivo treatment or diagnosis of malignancies or bacterial infections treated systemically, the compositions are typically administered by injection, and permitted sufficient time to home to the malignancies or infections or infective agents. Injection may be intravenous, subcutaneous, intramuscular, or intraperitoneal, and other administration may be orally, in some instances, or by other means of another approved mode of pharmaceutical administration. Injectables can be prepared in conventional forms, preferably with water as excipient.

As is known in the art, the treatment compositions may also contain minor amounts of nontoxic, auxiliary substances such as diluents and buffering agents and others. Fluorescence diagnostics are performed by visual or by fiber optic probes well known in the art.

As known in the art for the treatment of superficial tumors or skin disorders, the compositions may be topically administered using standard topical compositions involving typical excipients in the form of liquids, creams, gels, ointments, aerosols or others known in the art. In addition to in vivo use, compositions of this invention can be used in vitro to treat bacterial infectious agents. For illustration, not limitation, blood plasma or blood for transfusion can be treated with the compositions of this invention, and when desired, irradiated with appropriate light source as taught herein.

EXAMPLES—MATERIALS, APPARATUS, STOCK SOLUTIONS AND METHODS

Materials

All chemicals were used as received without further purification, except as noted. Commercially available Fe(III) TMPyP and TMPyP, as well as m-THPP and p-THPP, were purchased from Frontier Scientific Inc., USA. Iron (II) chloride and Iron (III) chloride were obtained from Flinn Scientific Inc., USA. DHN and Juglone were received from Acros Organics. Ultrapure $H_2O$ (18.2 M$\Omega$) was obtained from a U.S. Filter Corporation deionization system. Singlet oxygen sensor green (SOSG) was purchased from ThermoFisher Scientific Co., USA. 2-propanol was acquired from VWR Analytical, USA, and p-nitrophenol, $D_2O$, $NaN_3$, and methylene blue were acquired from Sigma Aldrich, USA.

Apparatus

Ultraviolet-visible (UV-vis) spectra were recorded by using an Agilent 8453 single beam diode array spectrometer (Agilent Technologies, USA, model 8453). Fluorescence spectra were recorded by using a Perkin-Elmer LS-55, Fluorescence Spectrometer (Perkin-Elmer, USA) at room temperature. All photosensitization experiments were carried out on a Rayonet Chamber Reactor equipped with sixteen 5750 Å lamps (The Southern New England Ultraviolet Co, USA, model RPR-100). Blue continuous-wave ("CW") laser (447 nm, 20 mW, 2.0 mm beam diameter), green CW laser (532 nm, 20 mW, 2.0 mm beam diameter), and CW laser (655 nm, 100 mW, Model: MRL-III-655-100 mW 15060452) were purchased from Dragon Lasers CO, China.

Stock Preparation and Methods

Standard solutions of TMPyP ($1.0 \times 10^{-3}$ M), iron (III) chloride ($1.0 \times 10^{-2}$ M), and iron (II) chloride ($1.0 \times 10^{-2}$ M) were prepared in ultra-pure $H_2O$ at room temperature under normal atmospheric conditions.

DHN ($1.0 \times 10^{-2}$ M) stock solution was prepared in a $CH_3CN:H_2O$ (9:1, v/v) mixture solvents at room temperature under normal pressure. Stock solutions containing (i) DHN ($4.2 \times 10^{-4}$ M) and TMPyP ($2.1 \times 10^{-5}$ M), (ii) Juglone ($4.2 \times 10^{-4}$ M) and TMPyP ($2.1 \times 10^{-5}$ M), and (iii) Fe(III) ($3.5 \times 10^{-4}$ M) and TMPyP ($2.1 \times 10^{-5}$ M) were added to individual samples.

For a typical experiment, microliter amounts of standard solutions were combined, for illustration not limitation, microliter amounts of a standard solution of Fe(III) solutions (30 μL of $1.0 \times 10^{-2}$ M) and DHN solution (36 μL of $1.0 \times 10^{-2}$ M) added into a cuvette containing 3 mL of solution TMPyP ($6.00 \times 10^{-6}$ M). Quartz cuvettes with 1 cm path-length and 3 mL volume were used for all measurements.

SOSG stock solutions were prepared by adding 33 μL of methanol to a 100 μg of SOSG sample to make a stock solution of ~5 mM. Experimental solutions comprising SOSG were prepared by combining 6 μL of SOSG stock solutions into 3 mL of aqueous solution of TMPyP ($6.0 \times 10^{-6}$ M) solution under normal atmospheric conditions. Experimental solutions of SOSG were then irradiated by a 532 nm CW laser and the fluorescence emissions at 525 nm (excitation at 504 nm, excitation slit 5 nm, emission slit 7 nm, speed 1000 nm/min, gain-medium) were recorded to monitor the production of $^1O_2$ in every 10 minutes for a duration of 60 minutes.

For singlet oxygenation of 1,5-dihydroxynaphthalene (DHN) by TMPyP in aqueous solution, a 3 mL solution of DHN ($1.2 \times 10^{-4}$ M) and TMPyP ($6.0 \times 10^{-6}$ M) was prepared by mixing 36 μL of $1 \times 10^{-2}$ M of DHN standard solution and 18 μL of $1 \times 10^{-3}$ M of TMPyP standard solution with ultrapure water. The solution was prepared at room temperature in an open atmosphere. Photooxygenation of samples was performed in a Rayonet photoreactor and monitored by recording a decrease of UV-vis absorption. For example, photoxygenation of DHN by TMPyP was performed in a Rayonet photoreactor for approximately twenty minutes at 28° C. and the photooxygenation of DHN was monitored by recording a decrease of UV-vis absorption of DHN at 301 nm for 20 minutes in 2 minutes intervals. The effect of metal ions on singlet oxygen generation was studied similarly except with the addition of microliter amounts of $M^{2+}$ or $M^{3+}$ ions ($1 \times 10^{-2}$ M) (positively charged cations with a +2 charge or a +3 charge) into a DHN/TMPyP aqueous solution.

Singlet Oxygen Quantum Yield ($\Phi_\Delta$) of TMPyP was determined using DHN ($1.2 \times 10^{-4}$ M) as a singlet oxygen quencher and methylene blue (MB) as a reference standard. A 3 mL solution of TMPyP ($6.0 \times 10^{-6}$ M) solution and MB ($1.0 \times 10^{-5}$ M) solution both of which contain DHN ($1.2 \times 10^{-4}$ M) were prepared. Each solution was irradiated with a 655 nm CW laser and the UV-vis spectrum of each solution was recorded at 1 min intervals for 5 minutes. The quantum yields were calculated with Equation 1 by using $\Phi_{\Delta(s)}$ of MB ($\Phi_\Delta = 0.52$) reported in the prior art.

$$\Phi_{\Delta(x)} = \Phi_{\Delta(s)} \times \frac{S_x}{S_s} \times \frac{F_s}{F_x} \qquad \text{Equation 1}$$

In Equation 1, S is the slope of the plot of the absorbance versus irradiation, and F is the absorption correction factor.

Method to assess bacteria inhibition examined in vitro effects with BL21 *E. coli*. The study of singlet oxygen generation from various aqueous solutions of DHN ($1.2 \times 10^{-4}$ M), Juglone ($1.2 \times 10^{-4}$ M), TMPyP ($6.0 \times 10^{-6}$ $6.00 \times 10^{-6}$ M), and Fe(III) ($1.0 \times 10^{-4}$ M), either alone or in various combinations, and resulting impact on bacteria were investigated through observed BL21 *E. coli* cell growth inhibition of irradiated versus a control sample containing only sterile water. Prior art procedure reported in Photochemistry and Photobiology 2010, 86 (4), 890-894 was followed to grow *E. coli* cells, even though other prior art procedures can be used. BL21 was selected because of availability. It is known that BL21 is deficient in Lon protease (cytoplasm) and OmpT protease (outer membrane) and does not carry the gene for T7 RNA polymerase. Luria Broth (LB)-Lennox formulation were allowed to grow in an incubator at 28° C. shaking at 250 rpm until the beginning of their exponential growth phase ($A_{600}$=0.2). For each experiment, one milliliter of the *E. coli* solution was centrifuged and washed with sterile water once. After removing washing liquid, the *E. coli* solutions were then re-suspended in 500.0 µL of sterile water and 200 µL of stock solutions of each of the following were added: (a) DHN ($4.2 \times 10^{-4}$ $4.20 \times 10^{-4}$ M), (b) Juglone ($4.2 \times 10^{-4}$ $4.20 \times 10^{-4}$ M), (c) Fe(III) ($3.5 \times 10^{-4}$ M) and TMPyP ($2.1 \times 10^{-5}$ $2.10 \times 10^{-5}$ M), (d) DHN ($4.2 \times 10^{-4}$ $4.20 \times 10^{-4}$ M) and TMPyP ($2.1 \times 10^{-5}$ $2.10 \times 10^{-5}$ M), (e) Fe(III) ($3.5 \times 10^{-4}$ M), DHN ($4.2 \times 10^{-4}$ M) and TMPyP ($2.1 \times 10^{-5}$ M), (f) Fe(III) ($3.5 \times 10^{-4}$ M), Juglone ($4.2 \times 10^{-4}$ M) and TMPyP ($2.1 \times 10^{-5}$ M), and TMPyP ($2.1 \times 10^{-5}$).

Controls of each sample were prepared similarly and kept covered to assure that no light was reacted with the TMPyP while other samples were irradiated in a Rayonet photoreactor for 10 minutes. After irradiation, the 700.0 µL samples were briefly vortexed and then 20.0 µL of each sample was spread evenly over individual petri dishes containing LB agar. The plates were inverted, then incubated at 28° C. for 48 hours. Observed effects of claimed treatment composition versus the various components of claimed composition on inhibition of *E. coli* cells to visually, not quantitatively, identify effectiveness.

For fluorescence study, three solutions of 3 mL volume were prepared. Study solution 1 (aqueous solution of TMPyP) was prepared by mixing 18 µL of $1.0 \times 10^{-3}$ M TMPyP with ultrapure water. Study solution 2 (aqueous solution of TMPyP and Fe(III) ions) was made by mixing 18 µL of $1.0 \times 10^{-3}$ M TMPyP and 30 µL of $1.0 \times 10^{-2}$ M iron(III) chloride with ultrapure water. Study solution 3 (aqueous solution of TMPyP and DHN) was prepared by mixing 18 µL of $1.0 \times 10^{-3}$ M TMPyP and 36 µL of $1.0 \times 10^{-2}$ M DHN with ultrapure water. Fluorescence emission was measured upon excitation of each solution at 423 nm with an excitation slit width of 10.0 nm and an emission slit width of 12.0 nm. Each experiment was carried out at room temperature and under normal atmospheric conditions.

Fluorescence quantum yield of the aqueous solution of TMPyP ($6.0 \times 10^{-6}$ M) was measured by prior art method described in The Journal of Physical Chemistry 1971, 75 (8), 991-1024 and Chemical Communications 2015, 51 (54), 10831-10834. Crystal violet ($1.0 \times 10^{-5}$ M) with a known $\Phi_F$=0.020 in water was used as a standard.

Optimization of hydrogen peroxide's concentration by DHN oxidation was evaluated by use of eight test solutions. Eight solutions of TMPyP ($6.0 \times 10^{-6}$ M), Fe(III) ions ($1.0 \times 10^{-4}$ M), and DHN ($1.2 \times 10^{-4}$ M) were prepared by mixing required amounts of TMPyP, Fe(III) ions, and DHN with ultrapure water at room temperature and under normal atmospheric conditions. To each solution a micromolar (µM) amount of $H_2O_2$ was added and the solution was left in dark for about 3 minutes. UV-vis spectrum was recorded before and after adding hydrogen peroxide to each solution to see the progress of DHN oxidation reaction. For each of the eight solutions, the following concentrations of hydrogen peroxide were added: 50 µM, 75 µM, 100 µM, 125 µM, 150 µM, 300 µM, 400 µM, and 500 µM.

Optimization of Fe(III) ion's concentration by DHN oxidation was evaluated by use of seven test solutions. Seven solutions of TMPyP ($6.0 \times 10^{-6}$ M), DHN ($1.2 \times 10^{-4}$ M), and $H_2O_2$ ($400 \times 10^{-6}$ M) were prepared by mixing required amounts of TMPyP, Fe(III) ions, DHN, and $H_2O_2$ with ultrapure water at room temperature and under normal atmospheric conditions. To each solution various Fe(III) ions (0.1 mM to 1.0 µM) amounts were added and then the solution was left in dark for about 3 minutes. UV-vis spectrum was recorded before and after adding hydrogen peroxide to each solution to see the progress of DHN oxidation reaction. For each test solutions, the following concentrations of hydrogen peroxide were added: $1.0 \times 10^{-4}$ M, $2.25 \times 10^{-5}$ M, $2.0 \times 10^{-5}$ M, $1.75 \times 10^{-5}$ M, $1.50 \times 10^{-5}$ M, $1.0 \times 10^{-5}$ M, and $1.0 \times 10^{-6}$ M.

Formation of oxygen gas from $H_2O_2$ was determined by visual observation. A 5 mL solution of TMPyP ($6.0 \times 10^{-6}$ M), DHN ($1.2 \times 10^{-4}$ M), and $H_2O_2$ ($1.0 \times 10^{-2}$ M) was prepared by mixing 30 µL of TMPyP ($1 \times 10^{-3}$ M), 60 µL of DHN ($1 \times 10^{-2}$ M), and 200 µL of $H_2O_2$ (2.6 M) with ultrapure water. The solution was then thoroughly mixed for 3 minutes before Fe(III) ions was added, then the solution was examined visually for $O_2$ gas formation. It was observed that oxygen gas ($O_2$) bubbles were formed immediately after the addition of 52 µL of Fe(III) ions (1 M) to aqueous solution of TMPyP, DHN, and $H_2O_2$ solution, and the bubble formation lasted more than 30 minutes.

Generation (or lack thereof) of singlet oxygen ($^1O_2$), hydroxyl radical (OH), and Juglone in aerobic and aerobic conditions under visible light irradiation was assessed in a series of tests of by various components (either individually or in several combinations and concentrations thereof) of claimed treatment compositions and variations of claimed treatment compositions were tested.

The observation of generation of ROS and formation of chemotherapeutic Jurlone or its derivatives is not only helpful to further the understanding of interactions of components, but teaches that these claimed treatment compositions may be of significance for singlet oxygen based clinical therapy wherein an abundant supply of singlet oxygen is required.

Results set forth herein below show that claimed treatment compositions and methods can facilitate multiple functions, under varying conditions (light, dark, aerobic, anaerobic) simultaneously of or in the same system. Surprisingly, it has been found that the claimed compositions enable enhanced ROS anti-cancer and diagnosis processes in the same system even though such processes are competitive.

Example 1

First, an experiment was performed in order to detect the generation of singlet oxygen ($^1O_2$) from TMPyP under visible light irradiation at 532 nm by using singlet oxygen sensor green (SOSG) in aqueous solution of TMPyP.

Figure 7:
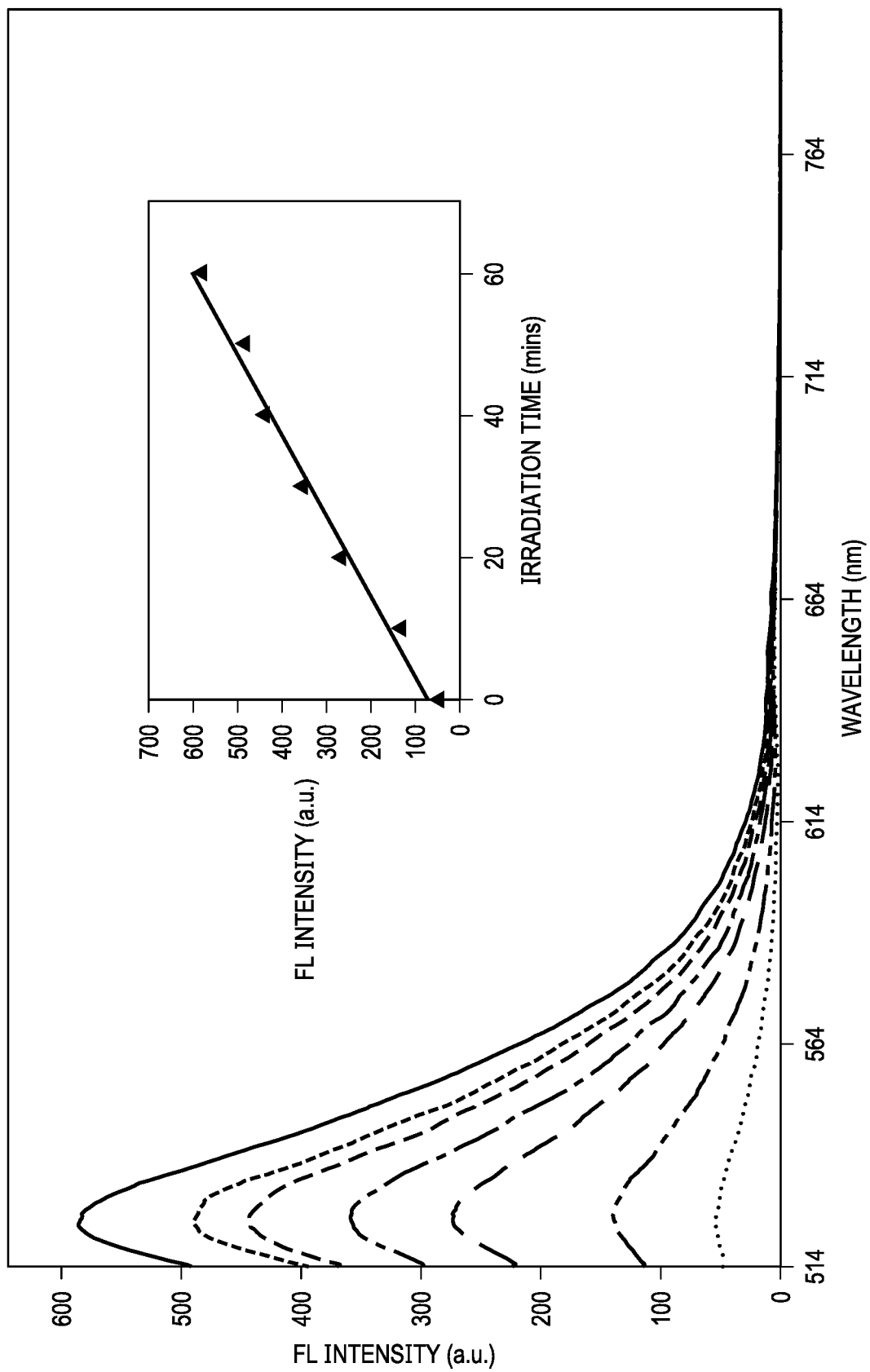
FIG. 7 shows in embedded window a reference analysis of fluorescence intensity of SOSG in response to increasing amount of irradiation time indicating generation of $^1O_2$ in aqueous solution and FIG. 7 main body is a reference analysis of plots emissions for TMPyP and SOSG in aqueous solution.

FIG. 7 shows in embedded window the fluorescence intensity of SOSG at 525 nm gradually increased with increasing amount of irradiation time indicating the generation of $^1O_2$ in aqueous solution. The fluorescence spectra of the SOSG emission intensity was recorded immediately after irradiation. As shown in FIG. 7 embedded window, the emission intensity increased significantly after 60 min of irradiation with 532 nm light. Other experiments indicate that the fluorescence emission intensity of SOSG in aqueous TMPyP solution greatly increased in $D_2O$ solvent compared to $H_2O$ and substantially decreased in presence of $NaN_3$. This data indicates that the aqueous solution of TMPyP generates $^1O_2$ upon irradiation with 532 nm light showing that TMPyP is useful as a singlet oxygen photosensitizer in aqueous environment.

FIG. 7 main segment shows a reference emissions plot for TMPyP ($6.0 \times 10^{-6}$ M) and SOSG in aqueous solution. Using a 532 nm laser irradiation of the sample was done at times 0 minutes (blue); 10 minutes (orange); 20 minutes (grey); 30 minutes (yellow); 40 minutes (light blue); 50 minutes (green); and 60 minutes (purple), in (b) The SOSG peak at 525 nm after 60 minutes of 532 nm laser irradiation recording the fluorescence spectra every 10 minutes. Each sample was ran using the following parameters; Ex WL: 423 nm; Start: 433 nm; End: 800 nm; Ex Slit: 10.0 nm; Em Slit: 12.0 nm; Speed: 1000 nm/min; Gain: High; Auto Lamp: on.

To determine the efficiency of TMPyP for singlet oxygen generation in aqueous solution, $^1O_2$ quantum yield ($\Phi_\Delta$) was calculated by using methylene blue as a standard with a known $\Phi_\Delta$ of 0.52. 1,5-dihydroxynaphthalene (DHN) has been used as a chemical probe to detect $^1O_2$ in solution and the reaction of DHN and $^1O_2$ is believed to be a very fast reaction and forms Juglone as a principal product. See in FIG. 2. Most importantly, the reaction of DHN and $^1O_2$ can be monitored by observing gradual decrease of the absorption of DHN peaks from 295 nm to 355 nm and so DHN can be used as a $^1O_2$ probe for $^1O_2$ quantum yield ($\Phi_\Delta$) measurement.

$$\Phi_{\Delta(x)} = \Phi_{\Delta(s)} \times \frac{S_x}{S_s} \times \frac{F_s}{F_x} \quad \text{Equation 1}$$

Above cited Equation 1 was followed to calculate $^1O_2$ quantum yield ($\Phi_\Delta$) for TMPyP, where S is the slope of the plot of the absorbance versus irradiation, and F is the absorption correction factor. The singlet oxygen quantum yield ($\Phi_\Delta$) of TMPyP was calculated to be 0.503, which is a little lower compared to prior art reports of 0.58 found in the prior art. However, a higher singlet oxygen quantum yield ($\Phi_\Delta$) for TMPyP such as 0.74 and 0.9 were also reported in the prior art.

Figure 2:
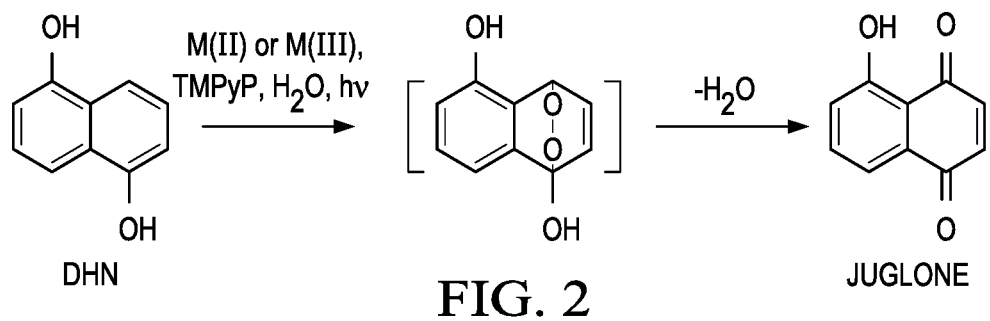
FIG. 2 is a schematic representation of a path for reaction of DHN with singlet oxygen to form Juglone.

As shown in FIG. 2, DHN can be photooxidized by $^1O_2$ to predominantly produce Juglone, 5-hydroxy-1,4-naphthoquinone, which is naturally found in walnuts. Over the last few years, Juglone has received greater recognition for its excellent pharmaceutical activities including antibacterial and antitumor properties. The recent success of Juglone-induced apoptosis of human breast cancer cells, colon cancer cells, and ovarian cancer cells has attracted a great deal of attention in the community and is therefore recognized as a chemotherapeutic agent against cancers.

Figure 8:
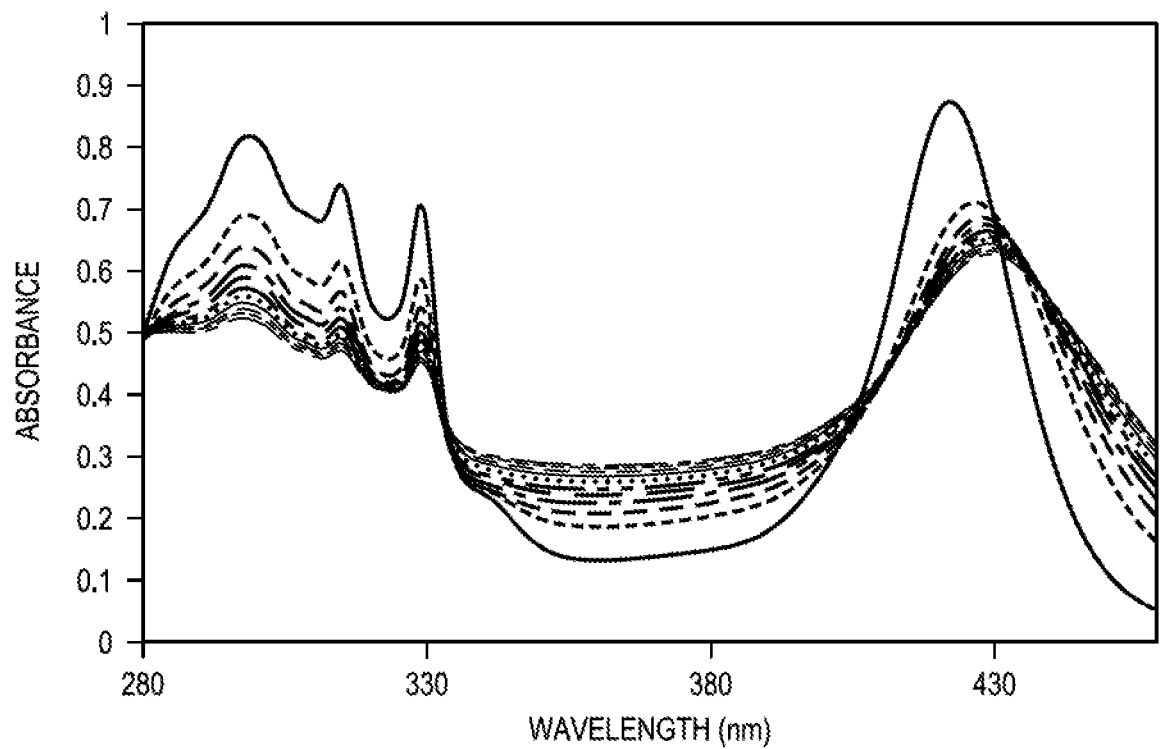
FIG. 8 is reference analysis of UV-vis spectra of TMPyP and DHN in aerobic, aqueous solution.

As shown in FIG. 8, upon irradiation of TMPyP and DHN solution with visible light, the various absorption peaks were found to decrease at 301, 317, and 331 nm during the course of reaction. The decrease of absorptions of DHN reveals that it is reacting with $^1O_2$ and producing Juglone, which usually absorbs at 423 nm. It is worthwhile to mention that the Soret band of TMPyP and the absorption maximum of Juglone appeared at 420 nm and 423 nm, respectively and thus, the increase of Juglone absorption at 423 nm was not seen upon irradiation of TMPyP/DHN aqueous solution.

Example 2

The effect of Fe(III) ions on photooxidation of DHN was investigated. Iron metal is an essential nutrient to the human body and it helps to operate many crucial functions including cell replication, metabolism, and growth in the mammalian cells. On the other hand, iron is a transition metal which has the capability to accept or lose electrons and take part in the free radical formation reactions.

Figure 9:
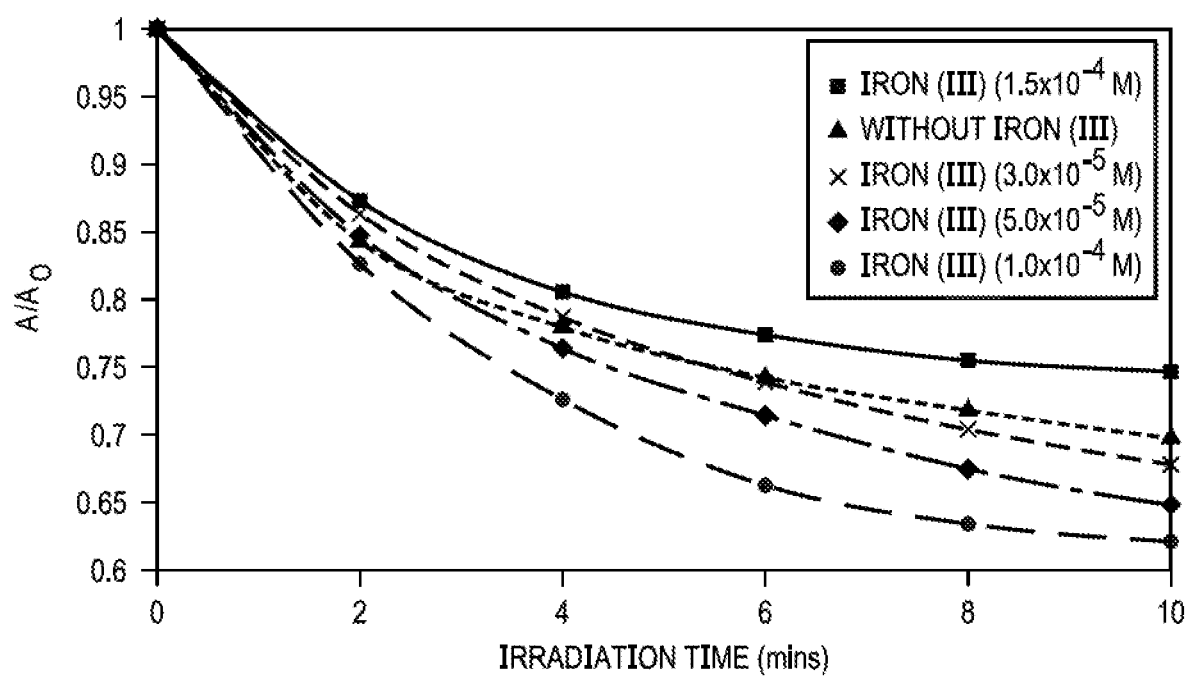
FIG. 9 is a plot of the rate of change of absorption of DHN monitored at 301 nm over 10 minutes as a function of irradiation time in aerobic conditions, conducted in the presence TMPyP without Iron (III) and at differing concentrations of Iron (III).

FIG. 9 is a plot of the rate of change over 10 minutes time of DHN monitored at 301 nm as a function of irradiation time in aerobic conditions. Experiments were conducted in the presence of DHN ($1.2 \times 10^{-4}$ M) and TMPyP ($6.0 \times 10^{-6}$ M), and (i) Iron (III) ($1.5 \times 10^{-4}$ M) (square); (ii) without Iron (III) (triangle); (iii) Iron (III) ($3.0 \times 10^{-5}$ M) (cross); Iron (III) ($5.0 \times 10^{-5}$ M) (diamond); and Iron (III) ($1.0 \times 10^{-4}$ M) (circle).

As shown in FIG. 9, the results of investigation of the effect of Fe(III) ions on photooxidation of DHN demonstrates that the rate of photooxidation of DHN by TMPyP depends on the concentration of Fe(III) ions in solution. The photooxidation of DHN by TMPyP in the presence of Fe(III) ions (monitored at 301 nm) was observed to follow pseudo first order kinetics and the rate constants were calculated by linear regression fitting of the experimental data (calculated absorbance values as $\ln(A_0)/(A)$ vs t, where $A_0$ is the absorbance at time 0, and A is the absorbance at time t).

Table 1 summarizes all rate constants of DHN photooxidation by TMPyP as a function of Fe(III) ions.

TABLE 1

| Solution of DHN and TMPyP with | Rate constant, $k_{obs}$ ($s^{-1}$) | $R^2$ |
| --- | --- | --- |
| No Fe (III) ions | $6.58 \times 10^{-4}$ | 0.8951 |
| $2.0 \times W^{-6}$ M Fe (III) | $3.90 \times 10^{-4}$ | 0.8321 |
| $4.0 \times 10^{-6}$ M Fe (III) | $5.27 \times 10^{-4}$ | 0.8507 |
| $3.0 \times 10^{-5}$ M Fe (III) | $7.15 \times 10^{-4}$ | 0.9505 |
| $5.0 \times 10^{-5}$ M Fe (III) | $7.98 \times 10^{-4}$ | 0.9495 |
| $1.0 \times 10^{-4}$ M Fe (III) | $9.43 \times 10^{-4}$ | 0.9422 |
| $1.5 \times 10^{-4}$ M Fe(III) | $5.68 \times 10^{-4}$ | 0.9018 |

The rate constant of DHN photooxidation by TMPyP was $6.58 \times 10^{-4}$ $s^{-1}$. Upon addition of 10 μL of $1.0 \times 10^{-3}$ M of Fe(III) ions, the rate of photooxidation of DHN by TMPyP decreased ($k=3.90 \times 10^{-4}$ $s^{-1}$) compared to metal free solution whereas a rapid increase of photooxidation of DHN by TMPyP was seen upon addition of increasing amount of Fe(III) ions. However, upon addition of 75 μL of $1.0 \times 10^{-2}$ M of Fe(III) ions, the rate of photooxidation of DHN by TMPyP significantly reduced ($k=5.68 \times 10^{-4}$ $s^{-1}$) indicating optimized reaction conditions, the photooxidation of DHN by TMPyP when Fe(III) concentration ranges from about 15 μL of $1.0 \times 10^{-2}$ M to 50 μL of $1.0 \times 10^{-2}$ M. A maximum rate of photooxidation of DHN by TMPyP was observed when Fe(III) ions concentration was about 50 μL of $1.0 \times 10^{-2}$ M ($k=9.43 \times 10^{-4}$ $s^{-1}$). Subsequent DHN photooxidation studies were targeted at 50 μL of $1.0 \times 10^{-2}$ M.

Example 3

To find the nature of produced ROS in the treatment composition (DHN/TMPyP/Fe(III) ions) solution, a series of control reactions were carried out using above described materials, solutions, apparatus and methods.

Figure 10:
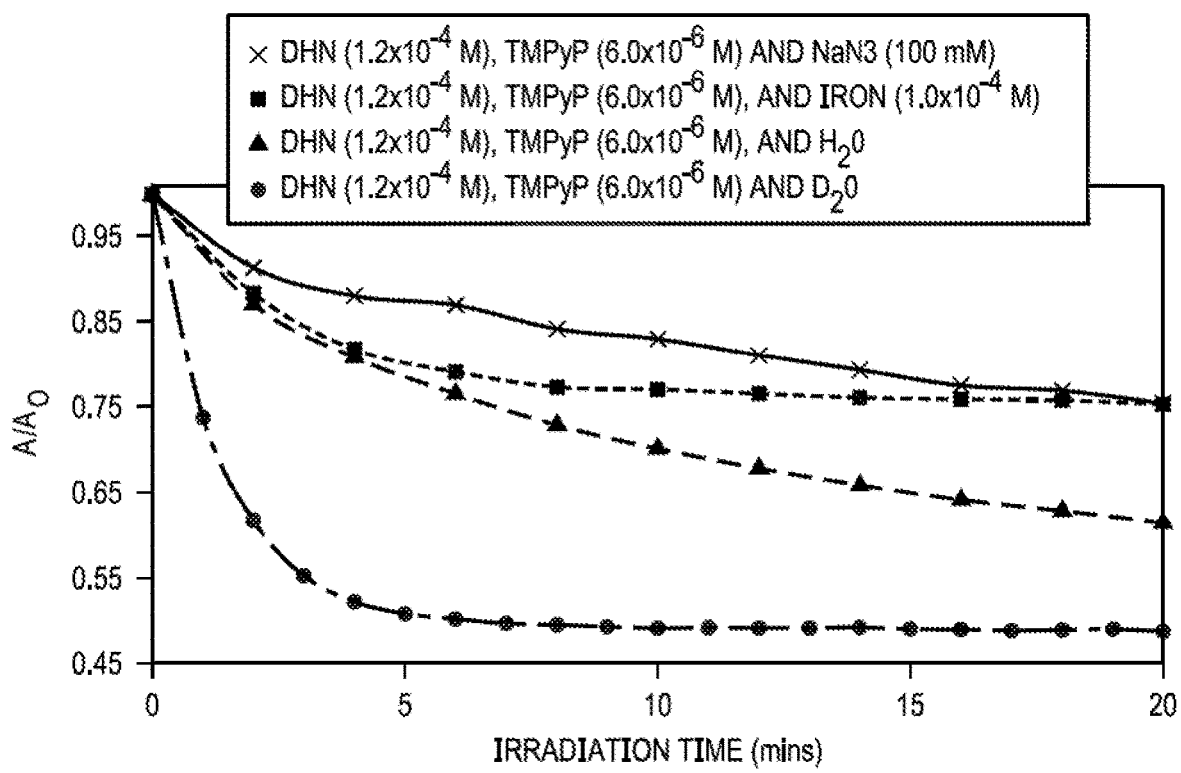
FIG. 10 is a plot of rate of change of absorption of DHN monitored at 301 nm as a function of irradiation time of various combinations and concentrations of DHN, TMPyP, $NaN_3$, Iron, $D_2O$, and $H_2O$.

Refer to FIG. 10, which is a plot of the rate of change over 20 minutes of DHN monitored at 301 nm as a function of irradiation time. Experiments were conducted in the presence of DHN ($1.2 \times 10^{-4}$ M), TMPyP ($6.0 \times 10^{-6}$ M) and NaN$_3$ (100 mM) (plotted as crosses); DHN ($1.2 \times 10^{-4}$ M), TMPyP ($6.0 \times 10^{-6}$ M) and D$_2$O (plotted as circles); DHN ($1.2 \times 10^{-4}$ M), TMPyP ($6.0 \times 10^{-6}$ M), and Iron ($1.0 \times 10^{-4}$ M) (plotted as squares); and DHN ($1.2 \times 10^{-4}$ M), TMPyP ($6.0 \times 10^{-6}$ M), and H$_2$O (plotted as triangles).

The rate of DHN photooxidation by TMPyP/Fe(III) ions was found to increase dramatically in D$_2$O compared to in H$_2$O indicating the presence of singlet oxygen ($^1O_2$), as shown in FIG. 10. Also, significantly slower photooxidation of DHN by TMPyP/Fe(III) ions was observed in the presence of NaN$_3$, a physical quencher of $^1O_2$, indicating the evidence of $^1O_2$ generation in solution.

Example 4

To determine hydroxyl radical ($\dot{O}H$) species, DHN was photooxidized by TMPyP/Fe(III) ions in the presence of $\dot{O}H$ radical's quencher, 2-propanol, using above described apparatus, materials and methods. Several prior art studies indicated that 2-propanol reacts very rapidly with hydroxyl radicals ($\dot{O}H$) ($1.3 \times 10^{-9}$ M$^{-1}$ s$^{-1}$) and produces 2-propanone product which can be detected by GC-MS spectrometer.

A series of photooxidation of DHN by TMPyP/Fe(III) was carried out with an excess of 2-propanol to verify the production of $\dot{O}H$ radicals. Qualitative analysis of GC-MS data showed that the photo-catalytic solution of TMPyP/Fe(III) ions was able to convert 2-propanol to its principal oxidation product, 2-propanone in the presence of DHN (an electron rich aromatic ring) in the solution. Additional experiments demonstrated that the solution of TMPyP/Fe(III) ions alone or in the presence of p-nitrophenol/salicylic acid (an electron deficient aromatic ring) failed to convert 2-propanol to 2-proanone indicating that the photo-catalytic solution of TMPyP/Fe(III) ions required DHN in order to produce $\dot{O}H$ under visible light irradiation. This data teaches that (DHN+TMPyP+Fe(III)) solution is equally capable of forming singlet oxygen ($^1O_2$) and hydroxyl radical ($\dot{O}H$) in aqueous solution under visible light irradiation.

Figure 11:
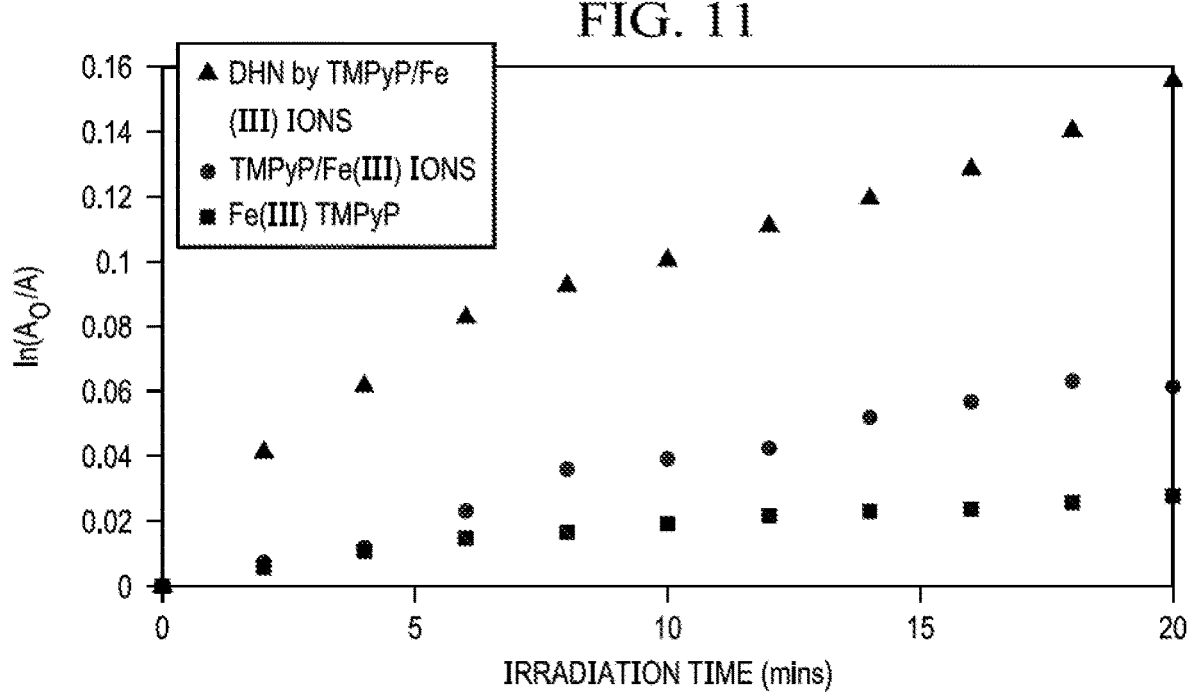
FIG. 11 is a plot of rate of change of absorption of DHN monitored at 301 nm over time in aerobic, aqueous solution with Fe(III)TMPyP, TMPyP and Fe(II), and TMPyP and Fe(III).

FIG. 11 shows a comparison of rates of the photooxidation of DHN by TMPyP/Fe(III) ions (plotted as triangles), TMPyP/Fe(II) ions (plotted as circles), and Fe(III)TMPyP (plotted as squares) (where iron ion is covalently bonded in the core of porphyrin ring) in aerobic aqueous environment. The obtained rate constants of photooxidation of DHN by TMPyP with Fe(II) ions and Fe(III)TMPyP were $5.23 \times 10^{-4}$ s$^{-1}$ and $4.67 \times 10^{-5}$ s$^{-1}$, respectively, whereas the rate constant of photooxidation for claimed compositions of DHN by TMPyP in the presence of Fe(III) ions is $6.58 \times 10^{-4}$ s$^{-1}$.

Table 2 shows rates of photooxidation of DHN ($1.2 \times 10^{-4}$ M) monitored at 301 nm as a function of irradiation time in the presence of Fe TMPyP ($6.0 \times 10^{-6}$ M), TMPyP ($6.0 \times 10^{-6}$ M) and iron (II) ($1.0 \times 10^{-4}$ M), and TMPYP ($6.0 \times 10^{-6}$ M) and iron (III) ($1.0 \times 10^{-4}$ M), respectively, in aerobic aqueous solution. $k_{obs}$ is the rate constant (s$^{-1}$) of the DHN decay kinetics.

TABLE 2

| Solution of DHN with | Rate Constant (s$^{-1}$), $k_{obs}$ | $R^2$ |
|---|---|---|
| Fe TMPyP | $5.5 \times 10^{-5}$ | 0.9679 |
| TMPyP and Iron (II) | $2.2 \times 10^{-5}$ | 0.9329 |
| TMPyP and Iron (III) | $1.1 \times 10^{-4}$ | 0.9342 |

This data clearly teaches that claimed treatment compositions comprising (DHN+TMPyP+Fe(III)) are potential therapeutic treatment compositions capable of producing three therapeutic agents, such as, singlet oxygen ($^1O_2$), hydroxyl radical ($\dot{O}H$), and Juglone or derivatives of Juglone in aqueous solution under visible light irradiation. The claimed therapeutic treatment composition can find potential applications for superficial cancer treatment or cancers where target is reachable with sufficient visible light and oxygen.

Example 5

In this Example 5, generation of hydroxyl radical ($\dot{O}H$), and Juglone by a variation of treatment composition in anaerobic condition under visible light irradiation was assessed using above described solutions, apparatus and methods.

Figure 3:
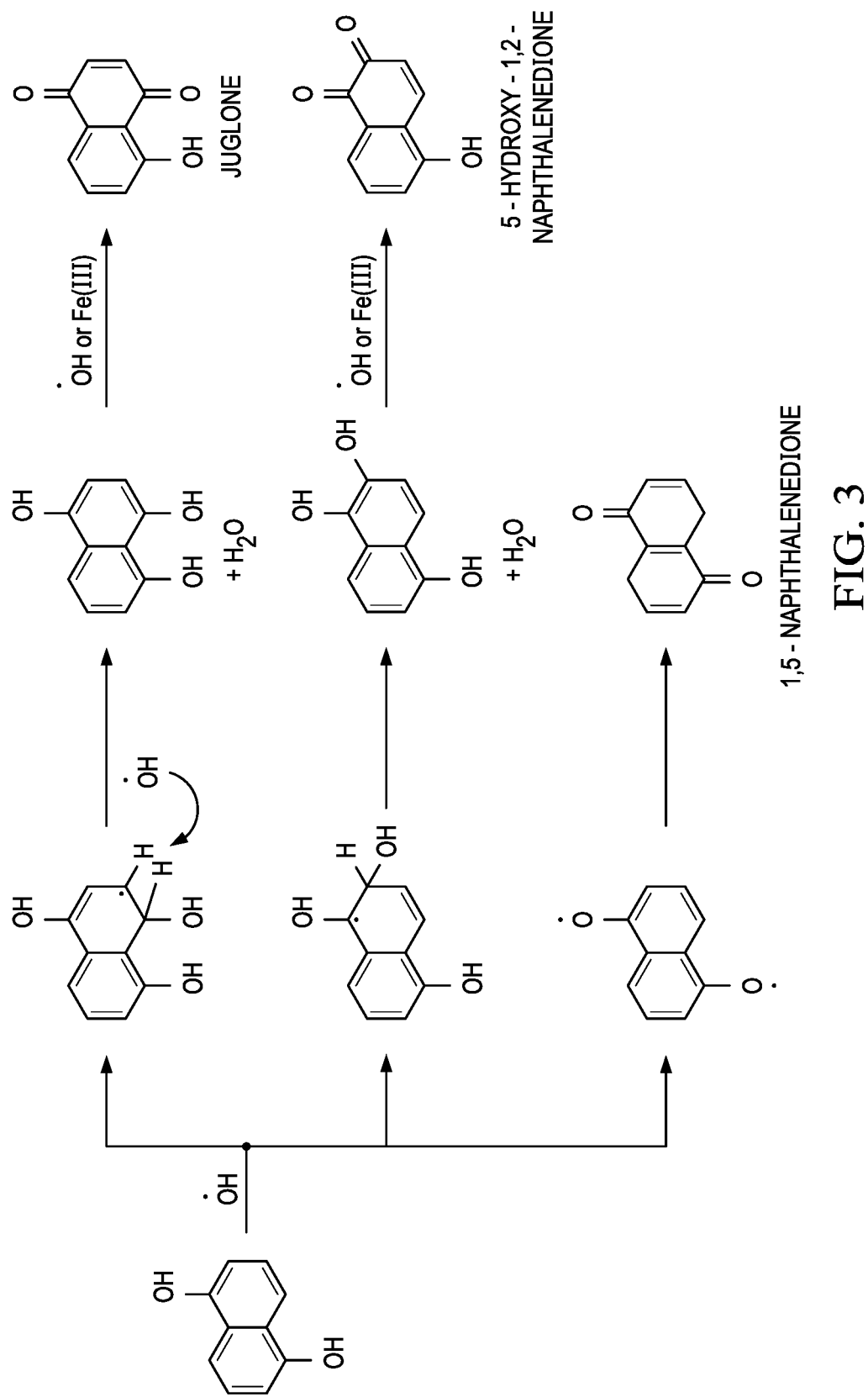
FIG. 3 is a schematic representation of multiple paths for oxidation of DHN by hydroxyl radical (ȮH), wherein Juglone is one possible reaction product.
Figure 4A:
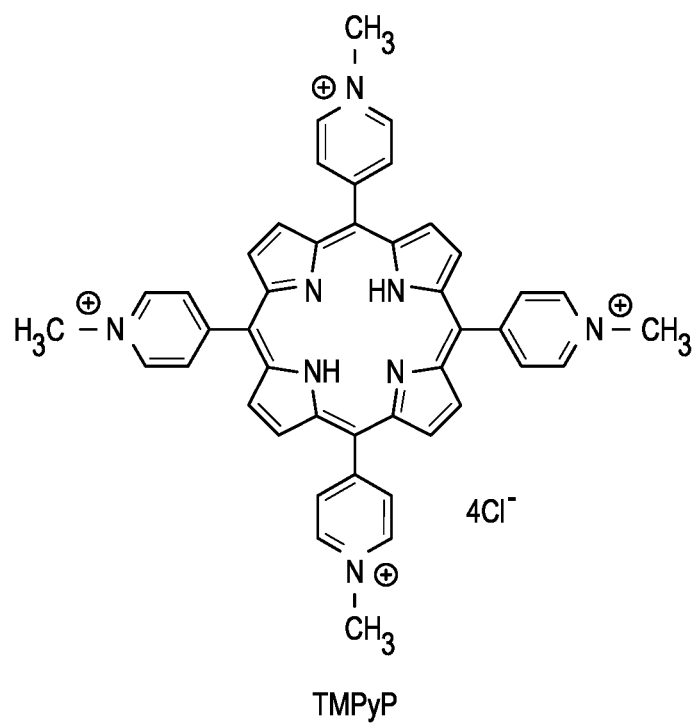
FIG. 4 is chemical structure drawing of commercially available TMPyP at FIG. 4A, commercially available iron bound Fe(III)TMPyP at FIG. 4B and p-THPP at FIG. 4C and m-THPP FIG. 4D.
Figure 4B:
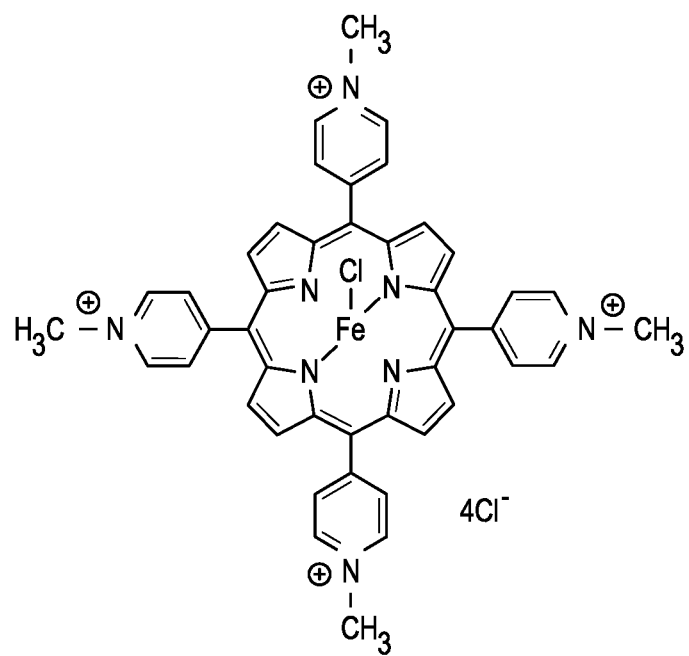
Figure 4C:
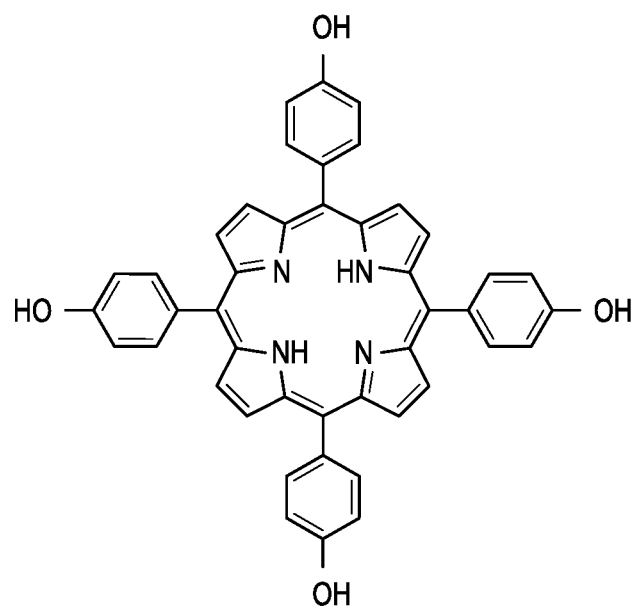
Figure 4D:
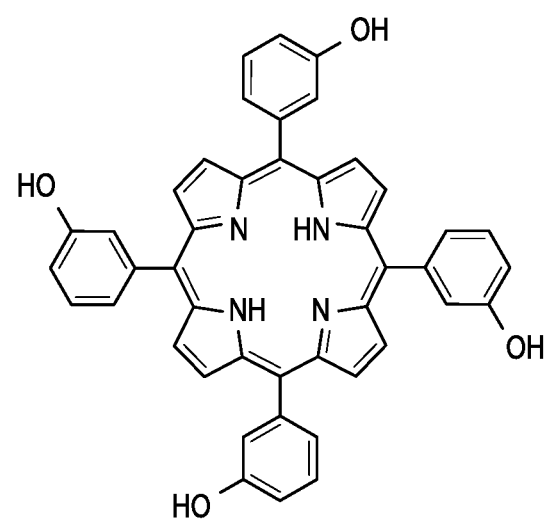
Figure 5A:
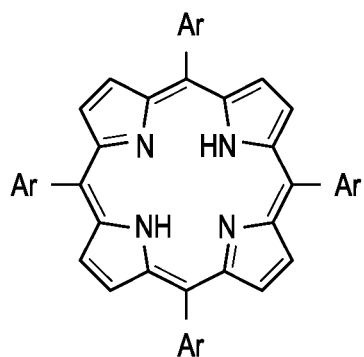
Figure 5A:
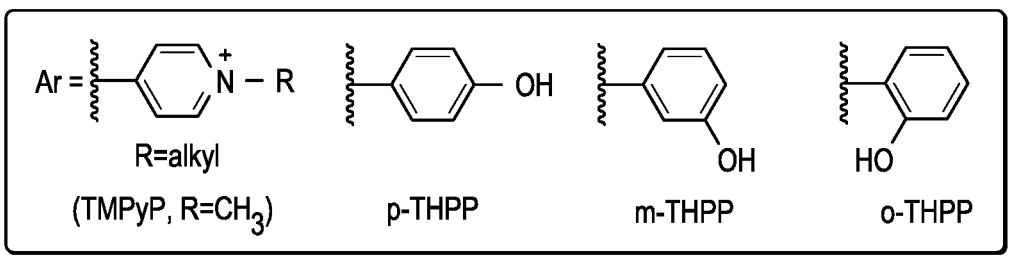
Figure 5B:
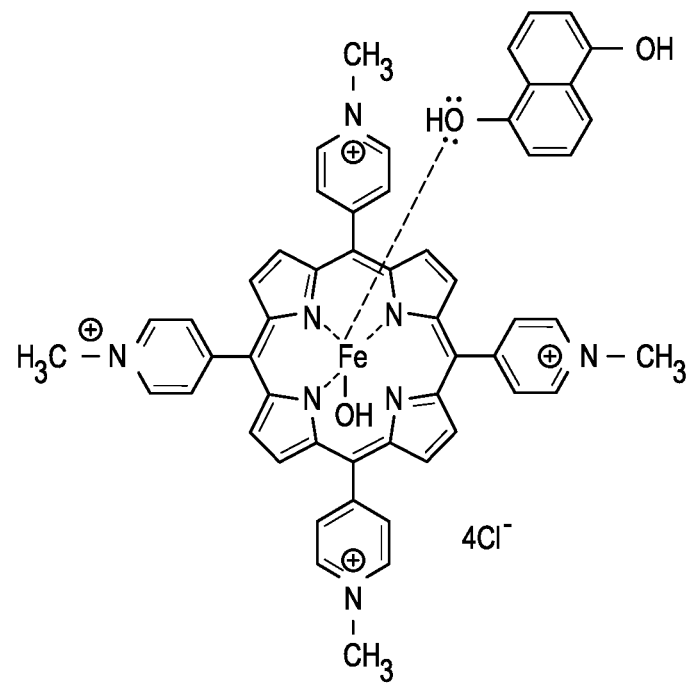
FIG. 5B shows one embodiment of (DHN+ TMPyP+Fe(III)) formed of DHN and TMPyP with Fe(III).

FIG. 3 shows three different proposed reaction schemes for reaction of DHN and hydroxyl radicals as well as the possible products such as Juglone product or other derivatives. The visible light photoreduction of Mn(III) and Fe(III) porphyrins such as commercially available Fe(III)TMPyP to generate hydroxyl radical ($\dot{O}H$) in aqueous medium has been studied extensively in the prior art.

The mechanisms are not very well understood, however, it is believed to be an intramolecular and it forms hydroxyl radical ($\dot{O}H$) via Equation 2, as shown below.

$$\text{Fe(III)(Por)(OH)} \xrightarrow{h\nu} \text{Fe(II)(Por)} + \dot{O}H \quad \text{Equation 2}$$

First, the treatment composition (DHN+TMPyP+Fe(III)) was compared against commercially available Fe(III) TMPyP and prepared TMPyP+Fe(II), all in presence of DHN, to determine if any or all can produce hydroxyl radical ($\dot{O}H$) in anaerobic condition. An aqueous solution of TMPyP and DHN was thoroughly purged with argon followed by irradiation with visible light. DHN's absorption at 301 nm was recorded in 2 minute intervals to monitor in situ production of $\dot{O}H$ in solution.

Figure 12:
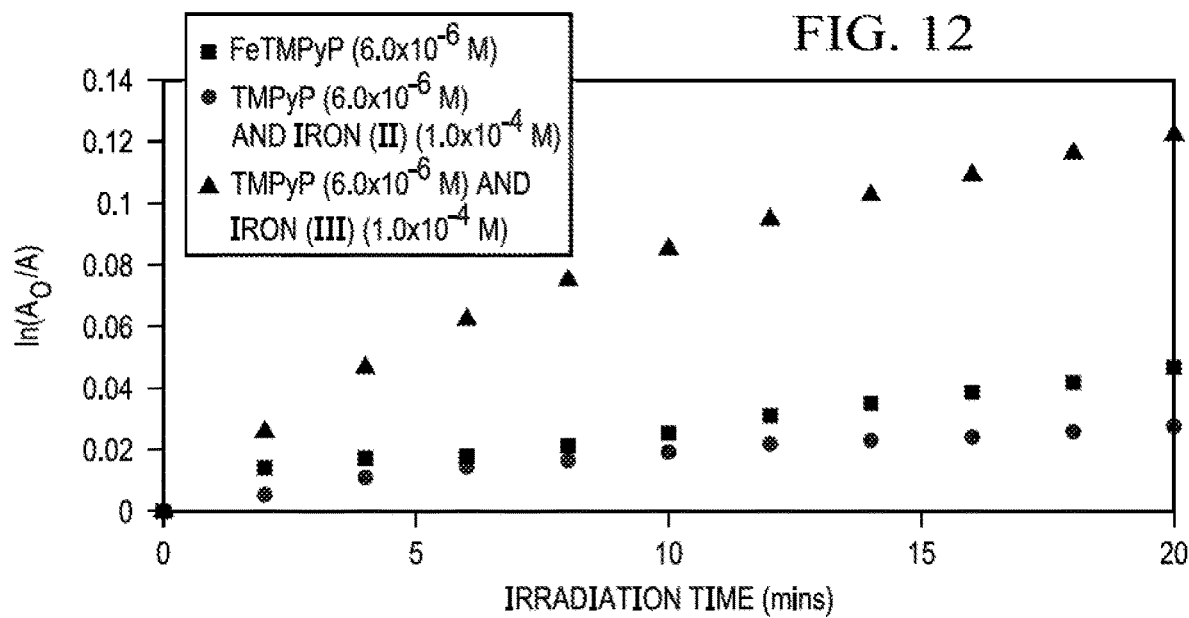
FIG. 12 is a plot of the rate of change of absorption of DHN monitored at 301 nm over time in anaerobic, aqueous solution with Fe(III)TMPyP, TMPyP and Fe(II), and TMPyP and Fe(III).

FIG. 12 shows a comparison of the rates of photooxidation of DHN by Fe(III)TMPyP (where iron is covalently bonded at the core of porphyrin) versus prepared TMPyP+Fe(II) and prepared TMPyP+Fe(III), in anaerobic aqueous environment.

FIG. 12 is a plot of the rate of change of absorption over 20 minutes for DHN ($1.2 \times 10^{-4}$ M) peak at 301 nm when irradiated with 20 minutes of light in solutions with FeTMPYP ($6.0 \times 10^{-6}$ M) (square); TMPYP ($6.0 \times 10^{-6}$ M) and iron (II) ($1.0 \times 10^{-4}$ M) (circle); and TMPYP ($6.0 \times 10^{-6}$ M) and iron (III) ($1.0 \times 10^{-4}$ M) (triangle) in anaerobic, aqueous solution.

Photo-oxidation of DHN was found to be very fast in TMPyP/Fe(III) solution (k=$1.12 \times 10^{-4}$ s$^{-1}$) whereas it was found to be two (2) times slower in Fe(III)TMPyP solution (k=$5.50 \times 10^{-5}$ s$^{-1}$) than what was observed in TMPyP/Fe (III) solution. The rate of DHN photooxidation was observed to be five times slower in TMPyP/Fe(II) solution ($k=2.17\times 10^{-5}$ s$^{-1}$) than in TMPyP/Fe(III).

Example 6

The influence of Fe(III) ions concentration on photooxidation of DHN in anaerobic conditions was assessed using above described solutions, apparatus and methods.

Figure 13:
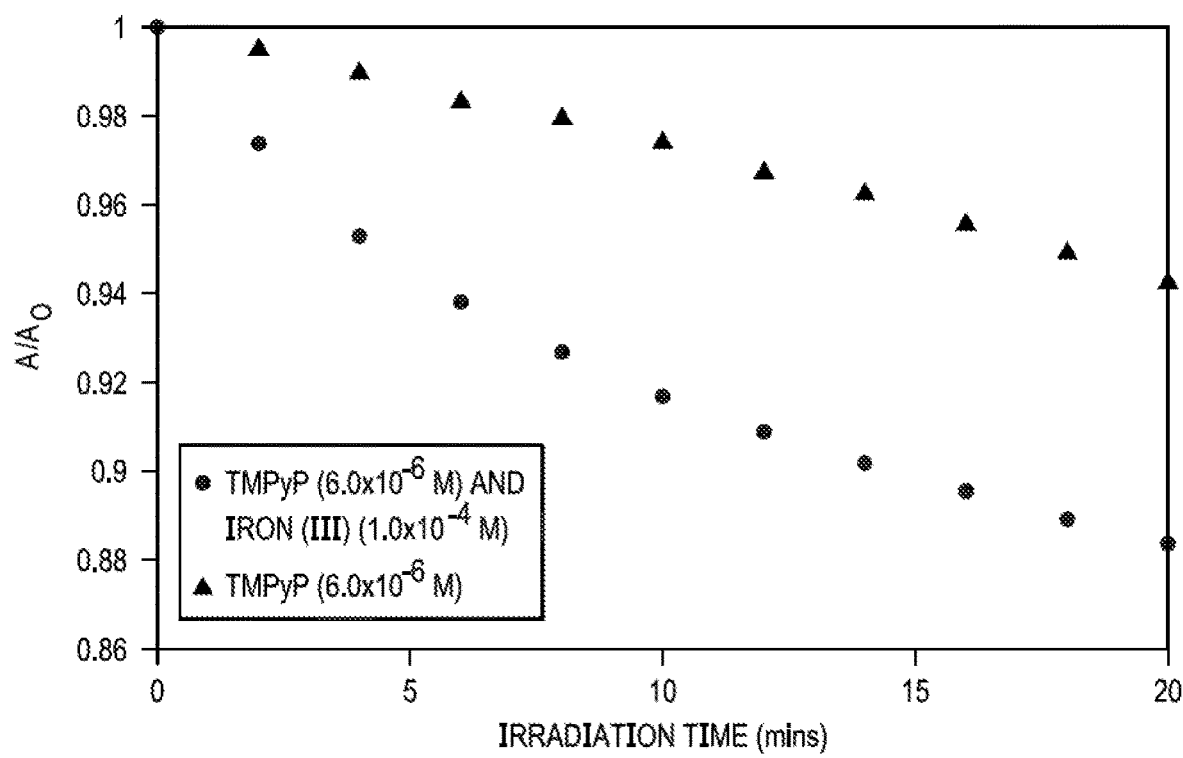
FIG. 13 shows the change in the absorbance peak (301 nm) of DHN in an anaerobic aqueous solution of just TMPYP and an anaerobic aqueous solution of TMPYP and Fe(III).

FIG. 13 shows the change in the absorbance peak (301 nm) of DHN ($1.20\times 10^{-4}$ M) in an anaerobic aqueous solution of just TMPYP ($6.0\times 10^{-6}$ M) (triangle) and an anaerobic aqueous solution of TMPYP ($6.0\times 10^{-6}$ M) and iron (III) ($1.0\times 10^{-4}$ M) (circle).

Figure 14:
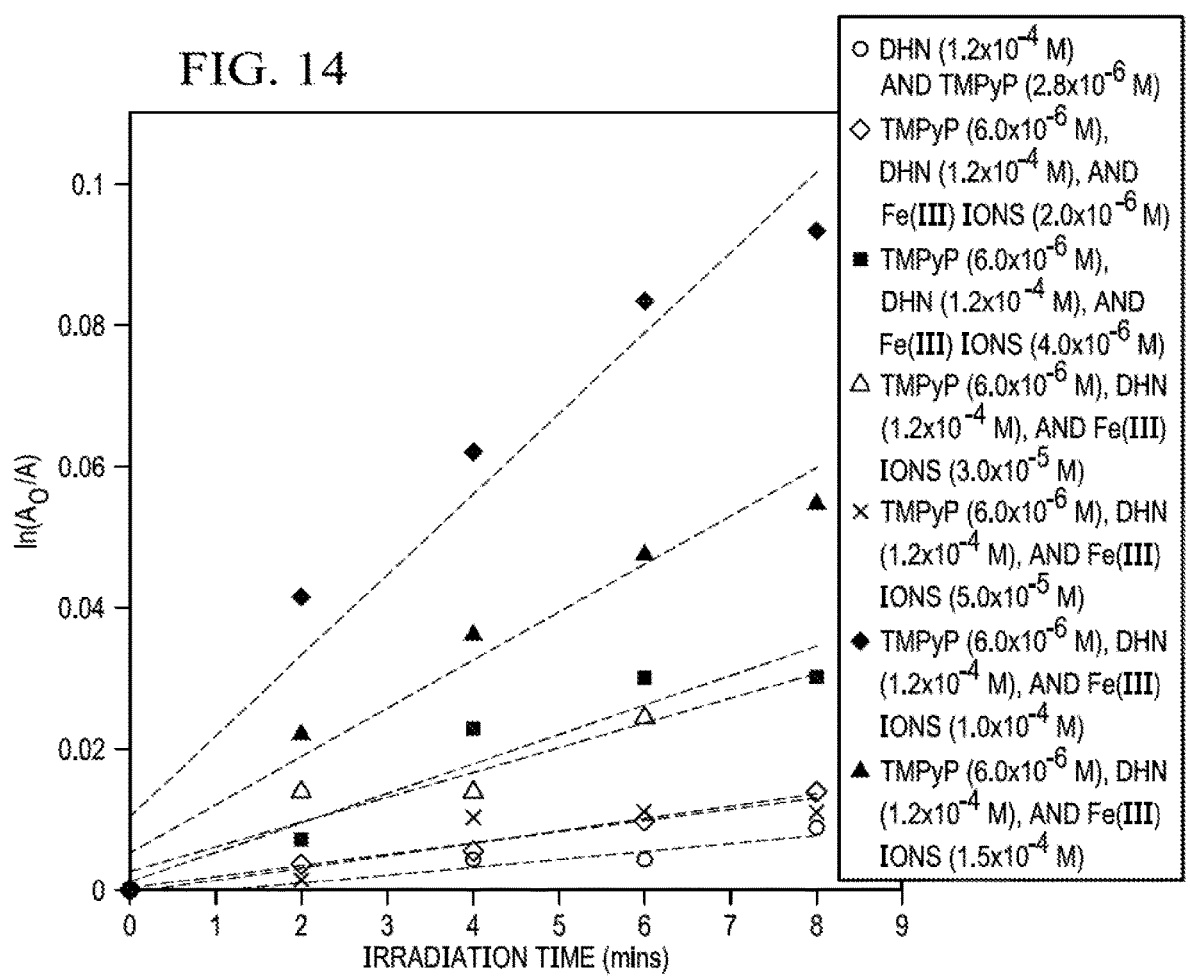
FIG. 14 shows the rate of change of DHN photooxidation by TMPyP as a function of Fe(III) ions in anaerobic aqueous solution.

As shown in FIG. 13, DHN experienced negligible photooxidation in the absence of Fe(III) ions in TMPyP solution, however, as shown in FIG. 14 in the presence of Fe(III) ions, the TMPyP and DHN solution showed a substantial photooxidation in anaerobic condition.

FIG. 14 shows the rate of change of DHN photooxidation by TMPyP as a function of Fe(III) ions in a thoroughly argon purged aqueous solution. FIG. 14 is a plot over 8 minutes of calculated absorbance of DHN (ln($A_0$)/(A)) monitored at 301 nm as a function of irradiation time in the presence of DHN ($1.2\times 10^{-4}$ M) and TMPyP ($2.8\times 10^{-6}$ M) (circles); TMPyP ($6.0\times 10^{-6}$ M), DHN ($1.2\times 10^{-4}$ M), and Fe(III) ions ($2.0\times 10^{-6}$ M) (lower diamonds); TMPyP ($6.0\times 10^{-6}$ M), DHN ($1.2\times 10^{-4}$ M), and Fe(III) ions ($4.0\times 10^{-6}$ M) (squares); TMPyP ($6.0\times 10^{-6}$ M), DHN ($1.2\times 10^{-4}$ M), and Fe(III) ions ($3.0\times 10^{-5}$ M) (empty triangles); TMPyP ($6.0\times 10^{-6}$ M), DHN ($1.2\times 10^{-4}$ M), and Fe(III) ions ($5.0\times 10^{-5}$ M) (crosses); TMPyP ($6.0\times 10^{-6}$ M), DHN ($1.2\times 10^{-4}$ M), and Fe(III) ions ($1.0\times 10^{-4}$ M) (upper diamonds); and TMPyP ($6.0\times 10^{-6}$ M), DHN ($1.2\times 10^{-4}$ M), and Fe(III) ions ($1.5\times 10^{-4}$ M) (filled triangles) in anaerobic aqueous solution.

Comparing FIG. 13 and FIG. 14, the disappearance of absorption of DHN by TMPyP with Fe(III) ions was observed to obey pseudo first order decay kinetics and the rate constants were calculated from the slope of experimental data (where in this instance, calculated absorbance values are as ln($A_0$)/(A) vs t, where $A_0$ is the absorbance at time 0, and A is the absorbance at time t).

Table 3 is a summary of all rate constants of DHN photooxidation by TMPyP as a function of Fe(III) ions.

TABLE 3

| Solution of DHN and TMPyP with | Rate constant, $k_{obs}$ (s$^{-1}$) | $R^2$ |
|---|---|---|
| No Fe (III) ions | $1.80 \times 10^{-5}$ | 0.8642 |
| $2.0 \times 10^{-6}$ M Fe (III) | $2.80 \times 10^{-5}$ | 0.9783 |
| $4.0 \times 10^{-6}$ M Fe (III) | $2.70 \times 10^{-5}$ | 0.8177 |
| $3.0 \times 10^{-6}$ M Fe (III) | $5.80 \times 10^{-5}$ | 0.9221 |
| $5.0 \times 10^{-5}$ M Fe (III) | $7.0 \times 10^{-5}$ | 0.9169 |
| $1.0 \times 10^{-4}$ M Fe (III) | $1.9 \times 10^{-4}$ | 0.9434 |
| $1.5 \times 10^{-4}$ M Fe (III) | $1.13 \times 10^{-4}$ | 0.9579 |

As depicted in FIG. 14, the rate constants of DHN photooxidation by TMPyP increased upon addition of increasing amount of Fe(III) ions and reached maximum value ($1.90\pm\times 10^{-4}$ s$^{-1}$) upon addition of 50 μL of $1.0\times 10^{-2}$ M. The rate constant of DHN photooxidation by TMPyP-generated ROS was noticed to get slowed down upon addition of 75 μL of $1.0\times 10^{-2}$ M of Fe(III) ions ($k=1.13\pm\times 10^{-4}$ s$^{-1}$) and found to be extremely slow in absence of any Fe(III) ions ($k=1.80\pm\times 10^{-5}$ s$^{-1}$) in solution.

Example 7

A series of control reactions were carried out to investigate the nature of ROS produced from variations of claimed treatment composition (DHN+TMPyP+Fe(III)) when photo-irradiated in anaerobic conditions. A direct photosensitization experiment of TMPyP/Fe(III) ions in argon purged, neutral aqueous solution showed no indication of generation of oxygen gas ($O_2$) (monitored by oxygen meter) over two hours of irradiation in neutral argon purged aqueous solution. Thus, the ROS species is believed to be something other than $^1O_2$, because $^1O_2$ is generally produced from a photosensitization reaction which involves a photosensitizer, oxygen, and visible light. It is not possible to have generated $^1O_2$ in solution in the absence of $O_2$ source. This was confirmed by carrying out same photosensitization reaction of TMPyP/Fe(III) ions in $D_2O$ medium and compared with what was observed in $H_2O$. No evidence of an increase of rate of the photooxidation of DHN by TMPyP with Fe(III) ions in $D_2O$ solvent was observed compared to $H_2O$ solvent, which indicates that there was no $^1O_2$ involvement in the photooxidation process.

To determine the hydroxyl radical (ȮH) species, a similar DHN photooxidation was carried out by using TMPyP/Fe (III) ions in the presence excess 2-propanol in argon purged aqueous solution. GC-MS analysis showed a conversion of 2-propanol to 2-propanone as a principal oxidation product. GC MS spectrometer failed to detect 2-proanone product when TMPyP/Fe(III) ions of treatment composition had no DHN present.

These results are not predictable and are unexpected.

The results surprisingly teach that ions from DHN+ TMPyP+Fe(III) compositions are capable of generating ȮH radicals in anaerobic aqueous environment. Likewise, anaerobic photooxidation of DHN by TMPyP/Fe(III) indicate that Juglone or its derivatives are forming in situ.

Example 8

Use of variations of claimed treatment compositions in dark conditions for removal of excess $H_2O_2$ and generation of hydroxyl radical (ȮH), and Juglone were evaluated using above described solutions, apparatus, and methods.

The efficient production of ROS in dark is a major challenge for current PDT against malignant cells. Since every photosensitization reaction uses visible light to sensitize dissolved oxygen ($O_2$) to singlet oxygen ($^1O_2$), the PDT method is completely ineffective in the absence of light.

Recently, Fenton reactions have been recognized as an effective, alternative, and promising selecting cancer treatment method. To evaluate efficacy of claimed treatment compositions under dark conditions, Fenton's-like reaction of a variation of claimed composition (DHN+TMPyP+Fe (III)) with $H_2O_2$ in dark conditions were evaluated.

Similar Fenton-like reactions were carried out to compare reactions with $H_2O_2$ in dark conditions in the presence of DHN by commercially available Fe(III)TMPyP and prepared TMPyP+Fe(II) against prepared TMPyP+Fe(III), thus comparing the first two with DHN against those of the latter claimed treatment compositions of (DHN+TMPyP+Fe(III)).

Figure 15:
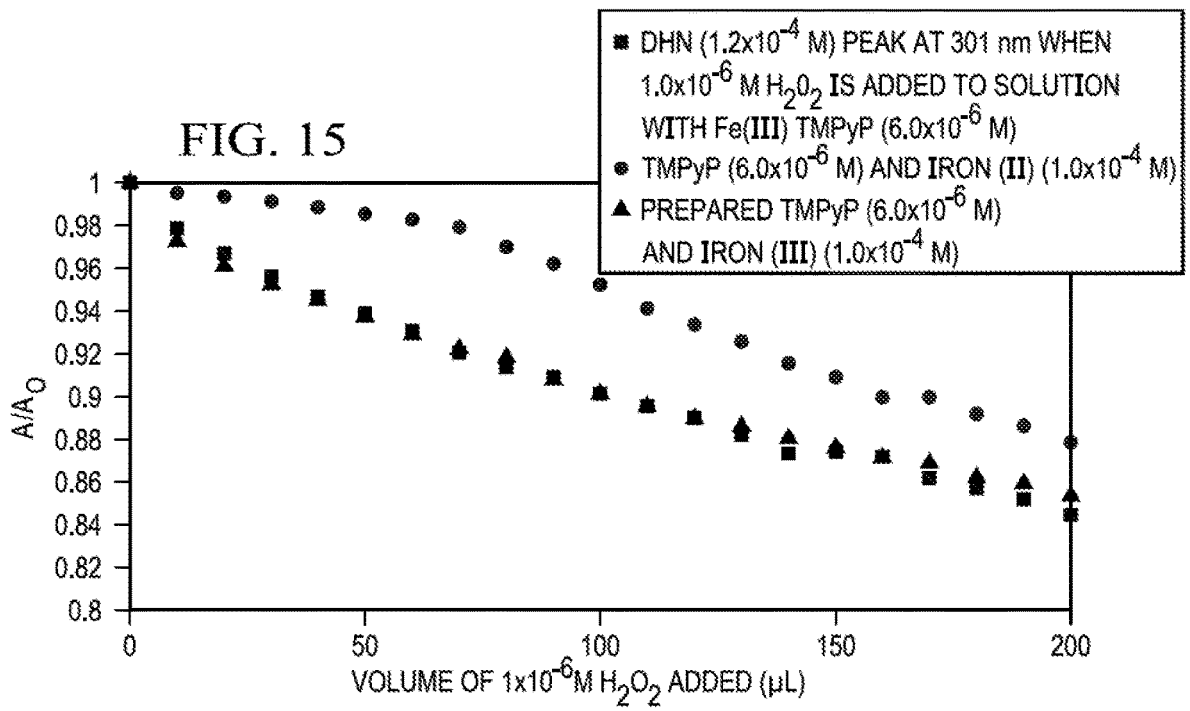
FIG. 15 shows DHN oxidation by commercially available Fe(III)TMPyP and prepared TMPyP+Fe(II) against prepared TMPyP+Fe(III) as a function of $H_2O_2$ concentration in aerobic aqueous solution under dark conditions.

FIG. 15 shows DHN oxidation by commercial Fe(III) TMPyP and prepared TMPyP/Fe(II) against prepared TMPyP+Fe(III) as a function of $H_2O_2$ concentration in aerobic aqueous solution under dark conditions. FIG. 15 is a plot of the rate of DHN change over volume of peroxide for DHN ($1.2\times 10^{-4}$ M) peak at 301 nm when $1.0\times 10^{-6}$ M $H_2O_2$ is added to solution with Fe(III)TMPyP ($6.0\times10^{-6}$ M) (plotted as squares); TMPyP ($6.0\times10^{-6}$ M) and Iron (II) ($1.0\times10^{-4}$ M) (plotted as circles); and prepared TMPyP ($6.0\times10^{-6}$ M) and Iron (III) ($1.0\times10^{-4}$ M) (plotted as triangles), forming a variation of claimed (DHN+TMPyP+Fe (III)) in aerobic, aqueous solution under dark conditions.

Figure 6A:
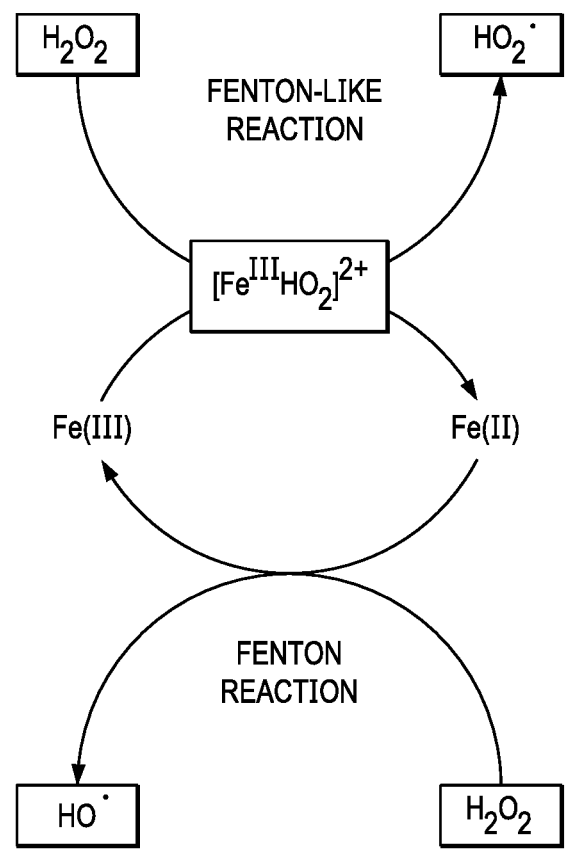
FIG. 6 is a schematic representation of three reaction schemes including production of $HȮ_2$, and evolution of $O_2$ gas and other materials wherein, in FIG. 6A Scheme 3(a) shows possible reactions via a Fenton-like reaction, in FIG. 6B Scheme 3(b) shows possible reactions from $HȮ_2$, and in FIG. 6C Scheme 3(c) shows possible reactions from ȮH.

DHN oxidized more rapidly and almost at the same rates in the presence of Fe(III)TMPyP prepared TMPyP+Fe(III) and compared to TMPyP/Fe(II). As normally observed in Fenton-like reaction, $H_2O_2$ reacts with Fe(III) ions and forms Fe(III)-peroxo complexes, which later decomposes into Fe(II) and $H\dot{O}_2$ radicals. The produced Fe(II) ions then reacts with $H_2O_2$ to produce reactive $\dot{O}H$ radicals via Fenton reaction, which subsequently reacts with DHN. Similarly, the produced $H\dot{O}_2$ radicals react with other $H\dot{O}_2$ or Fe(III) ions or Fe(II) ions and produce $O_2$, Fe(II) and $O_2$, and $[Fe^{III}HO_2]^{2+}$, respectively, see in FIG. 6A Scheme 3(a).

These test results are not expected but teach that a Fenton-like reaction of $H_2O_2$ with prepared TMPyP+Fe(III) was capable of generating $\dot{O}H$ in situ and oxidizing DHN in dark conditions and forming in situ Juglone or derivatives of Juglone. Control reactions of DHN with TMPyP and $H_2O_2$ and of DHN with $H_2O_2$ alone revealed no detectable DHN oxidation in dark providing unexpected teaching that Fe(III) ion and $H_2O_2$ are the required reagents for the generation $\dot{O}H$ radicals in aqueous solution and support effectiveness of claimed compositions of (DHN+TMPyP+Fe(III)).

Example 9

For variations of the claimed treatment composition, the optimum concentration of $H_2O_2$ and Fe(III) ions for effective Fenton-like reaction mediated $\dot{O}H$ generation in aqueous solution under dark condition was determined using above described solutions, apparatus, and methods.

Figure 16A:
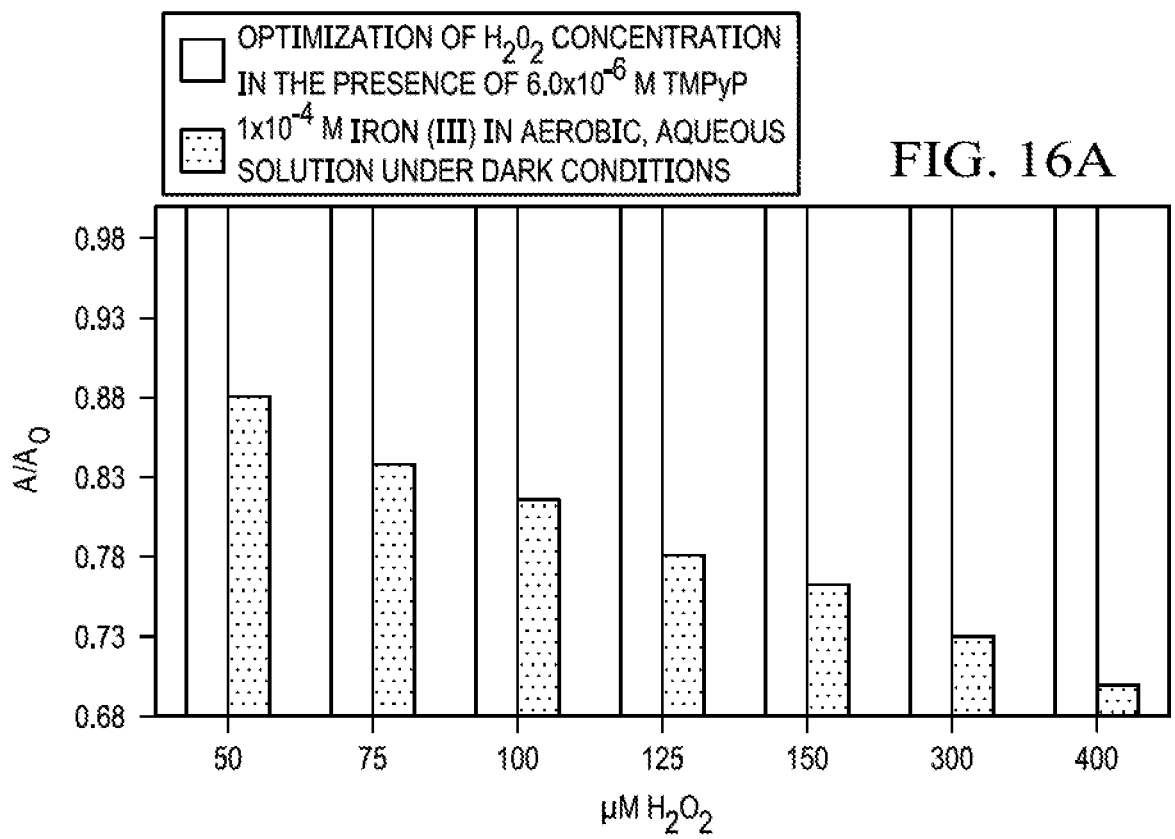
FIG. 16 shows in FIG. 16A optimization of $H_2O_2$ concentration in the presence of TMPyP and Fe(III) in aerobic, aqueous solution under dark conditions and in FIG. 16B UV-vis spectra of DHN by $H_2O_2$ in the presence of TMPyP and Fe(III) at three different $H_2O_2$ concentrations.
Figure 16B:
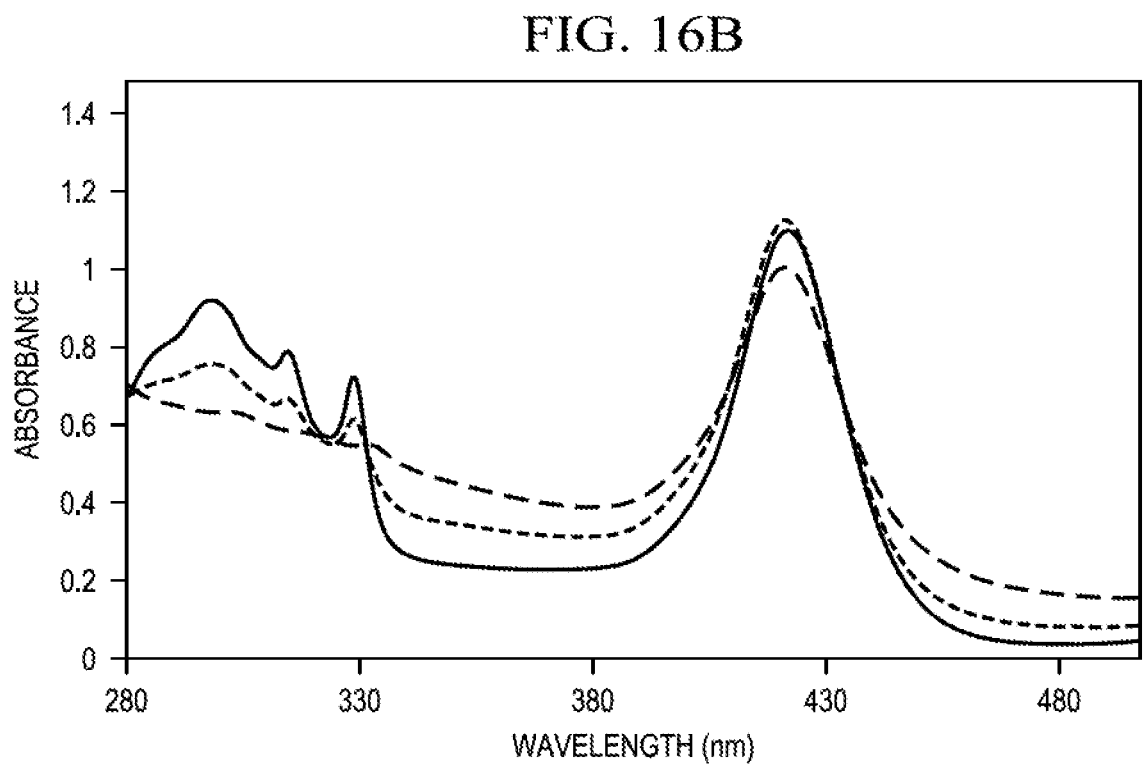

FIG. 16A shows (a) optimization of $H_2O_2$ concentration in the presence of $6.0\times10^{-6}$ M TMPyP and $1\times10^{-4}$ M iron (III) in aerobic, aqueous solution under dark conditions and in FIG. 16B the UV-vis spectra of DHN oxidation by $H_2O_2$ in the presence of TMPyP and Fe(III), for $H_2O_2$ concentrations of 0 μM at solid line, 400 μM at long dash line, and 50 μM $H_2O_2$ at short dash line. In FIG. 16A, each un-shaded left parallel bar is $A_0$ and each right shaded parallel bar is A, where $A_0$ is the absorbance at time 0, and A is the absorbance at time t for each sample.

Figure 17A:
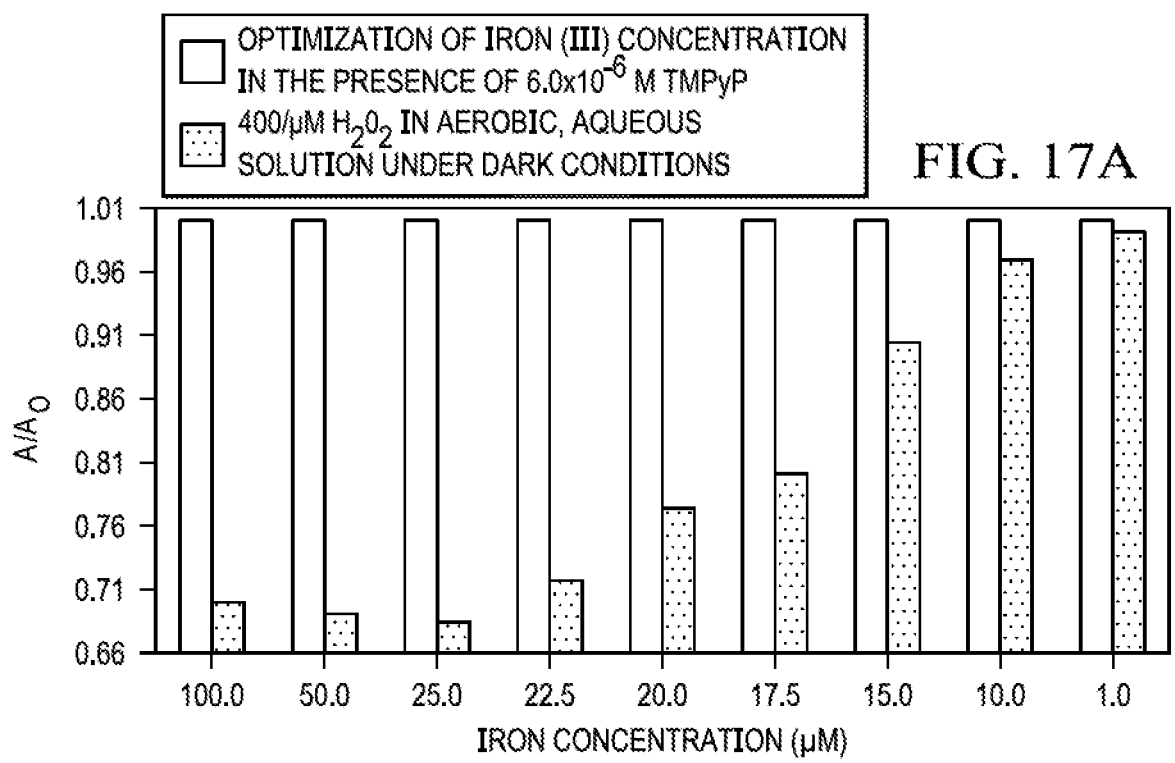
FIG. 17 shows in FIG. 17A optimization of Fe(III) concentration in the presence of 400 μM $H_2O_2$ and TMPyP in aerobic, aqueous solution under dark conditions and in FIG. 17B UV-vis spectra of DHN oxidation by $H_2O_2$ in the presence of TMPyP and Fe(III) ions for various Fe(III) concentrations.
Figure 17B:
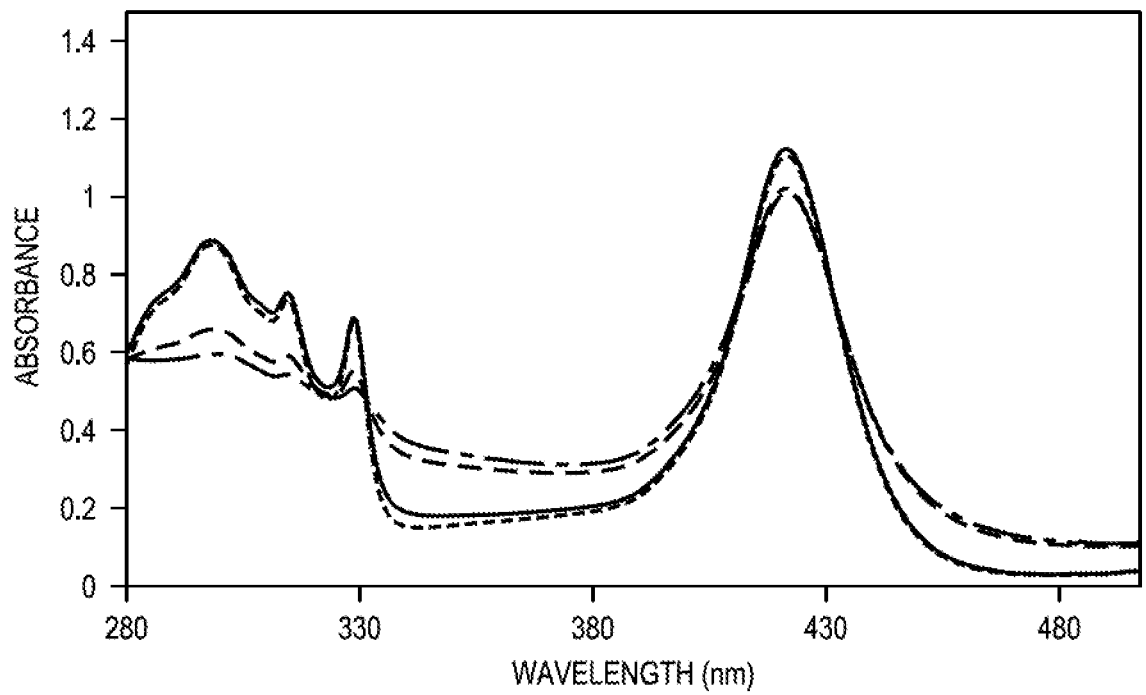

FIG. 17A shows optimization of iron (III) concentration in the presence of $6.0\times10^{-6}$ M TMPyP and 400 μM $H_2O_2$ in aerobic, aqueous solution under dark conditions and in FIG. 17B the UV-vis spectra of DHN oxidation by $H_2O_2$ in the presence of TMPyP and Fe(III) ions. Solid line is for (0 μM $H_2O_2$ and 25 μM Fe(III)), small dash line is for (400 μM $H_2O_2$ and 1.0 μM Fe(III)), medium dash line for (400 μM $H_2O_2$ and 20 μM Fe(III)), and long dash line is for (400 μM $H_2O_2$ and 25 μM Fe(III)). In FIG. 17A each left un-shaded parallel bar is $A_0$ and each right shaded parallel bar is A, where $A_0$ is the absorbance at time 0, and A is the absorbance at time t for each sample.

FIG. 16A shows that the absorption of DHN at 301 nm decreases when the solution of (DHN+TMPyP+Fe(III)) is treated with varying amounts of $H_2O_2$ and the Fe(III) ions ($1\times10^{-4}$ M Fe(III) ions) and TMPyP ($6.6\times10^{-6}$ M) are kept constant. A maximum decrease of absorption of DHN at 301 nm is observed when 400 μM $H_2O_2$ was used, as per FIG. 16B.

Similarly, experiments were carried out using above described solutions, apparatus, and methods to seek an optimum concentration of Fe(III) ion by varying the concentration of Fe(III) while the concentration of TMPyP ($6.6\times10^{-6}$ M), DHN ($1.0\times10^{-4}$ M), and $H_2O_2$ (400 μM) were kept constant.

FIG. 17A and FIG. 17B shows absorption of DHN at 301 nm changes with a varying concentrations of Fe(III) ions concentration. A maximum decrease of absorption of DHN was observed when Fe(III) concentration was 25 μM per see FIG. 17A and FIG. 17B.

This Example 9 data is unexpected, and among other discoveries, teaches optimum iron concentrations for variations of the claimed treatment concentration.

Example 10

Prior art literature reports that the catalase enzyme plays an important, protective role in normal cells to prevent the accumulation of toxic $H_2O_2$ by converting it to $H_2O$ and $O_2$. However, an increasing amount of literature reports that cancer cells produce more $H_2O_2$ compared to normal cells due to rapid proliferation of cancer cells and the level of catalase at normal physiological concentrations is not sufficient enough to fully detoxify $H_2O_2$ and protect cells from $H_2O_2$.

Figure 6B:
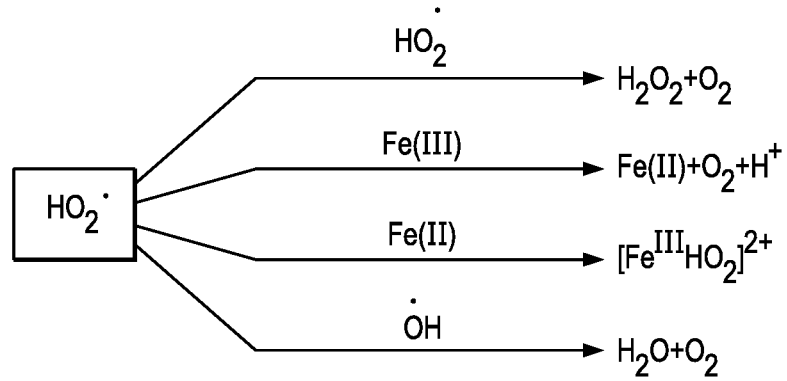

To mimic catalase type activity for the claimed treatment compositions, several oxygen evolution reactions were carried out by using variations of the treatment composition of DHN+TMPyP+Fe(III) with varying concentration of Fe(III) ions and $H_2O_2$ in aqueous solution (pH=5.5) at room temperature under normal atmospheric conditions. $O_2$ bubbles in solution were observed and documented. Further exploration of $O_2$ gas generation experiments demonstrated that the reaction is highly dependent upon the presence of both Fe(III) and $H_2O_2$. No evidence of sludge of Fe(OH)$_3$ was observed from $O_2$ evolution experiment of treatment composition with $H_2O_2$. However, an $O_2$ evolution experiment of FeTMPyP with $H_2O_2$ produced sludge of brown precipitate under identical reaction conditions. The pH of the solution of Fe(III)/TMPyP was measured and it showed that the solution's pH gradually decreased from 5.5 to 3.0 upon addition of $H_2O_2$ The change in pH teaches that Fe(III) ions reacted with $H_2O_2$ to form $O_2$ gas and released protons ($H^+$) into the solution. As seen in FIG. 6 Scheme 3, a Fenton-like reaction of Fe(III) with $H_2O_2$ produces $H\dot{O}2$, which subsequently reacts with another $H\dot{O}2$, Fe(III) ions and $\dot{O}H$ and produce $O_2$ as a principal product. See FIG. 6B Scheme 3(b) for $O_2$ evolution reactions.

Oxygen generation evidence teaches that a Fenton-like reaction of the claimed treatment composition is capable of detoxifying excess $H_2O_2$ to $O_2$ under dark conditions without forming any Fe(OH)$_3$ sludge in aqueous solution and with that capability can protect cells from excess toxic $H_2O_2$. The claimed treatment composition has a surprising and remarkable application in the elimination of cancer cells' hypoxic environments by directly producing $O_2$ gas via Fenton-like reactions in dark conditions.

Example 11

Figure 18:
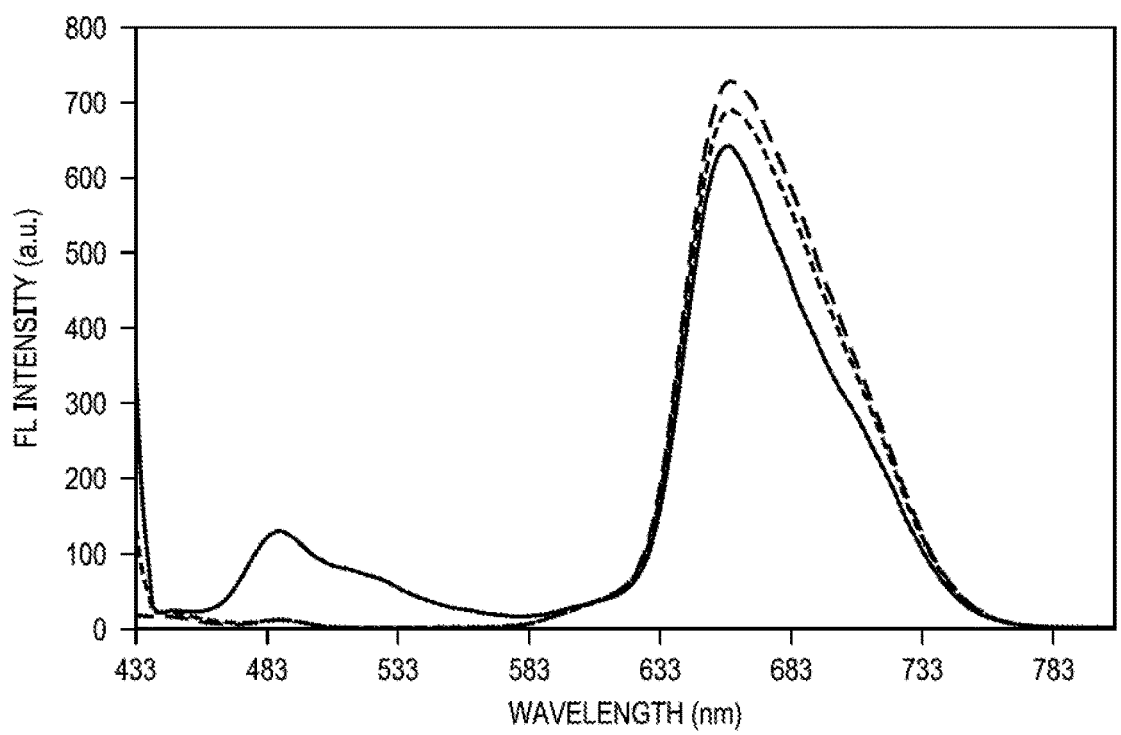
FIG. 18 is a plot of emissions for combination of TMPyP, Fe(III), and DHN in aqueous solution and shows the treatment composition is useful for image-guided PDT applications.

Fluorescence properties were studied to determine the potential of the claimed treatment solution for image-guided photodynamic diagnosis. FIG. 18 shows comparative emission spectra. Each was run using the following parameters; Ex WL: 423 nm; Start: 433 nm; End: 800 nm; Ex Slit: 10.0 nm; Em Slit: 12.0 nm; Speed: 1000 nm/min; Gain: High; Auto Lamp: on; T FIG. 18 long dash line is $6.0\times10^{-6}$ M TMPyP alone. FIG. 18 short dash line is $6.0\times10^{-6}$ M TMPyP with $1.0\times10^{-4}$ M Iron (III). FIG. 18 solid line is 6.0×10$^{-6}$ M TMPyP, 1.0×10$^{-4}$ M iron (III), and 1.2×10$^{-4}$ M DHN, the treatment composition.

The study teaches that, upon addition of Fe(III) ions to only a TMPyP solution, a very negligible change of fluorescence intensity of TMPyP was observed whereas upon addition of DHN to TMPyP with Iron (III) a slight reduction of fluorescence intensity of TMPyP was observed.

Then the fluorescence quantum yield ($\Phi_F$) of TMPyP was calculated by using Equation 3 and crystal violet (1.0×10$^{-5}$ M) as a standard with $\Phi_F$=0.020 in water, fluorescence quantum yield known from the prior art.

$$\Phi_{F(x)} = \Phi_{F(s)} \times \frac{A_s}{A_x} \times \frac{F_x}{F_s} \times \left(\frac{n_x}{n_s}\right)^2 \qquad \text{Equation 3}$$

where in Equation 3, A is the absorbance, F represents the area under the emissions curve, and n is the refractive index of the solvent used. The $\Phi_F$ of TMPyP was calculated to be 0.0139, which is almost comparable with prior art literature value of 0.016.

The experimental data obtained teaches that TMPyP fluoresces in aqueous media and unexpectedly shows that fluorescence intensity is not severely affected by the presence of Fe(III) ions and DHN. Thus, the claimed treatment composition (DHN+TMPyP+Fe(III)) is useful for image-guided PDT applications.

Example 12

Tests were conducted, using above described materials, apparatus and methods, to evaluate generation of hydroxyl radical (ȮH) and Juglone by use of m-THPP and p-THPP with DHN and Fe(III) to determine if m-THPP and p-THPP were effective in anaerobic conditions with DHN and Fe(III) in a manner similar to TMPyP. That is, formulated meso-tetra(m-hydroxyphenyl)porphine (m-THPP) with DHN and Fe(III) ions samples and formulated meso-tetra(p-hydroxyphenyl)porphine (p-THPP) with DHN and Fe(III) samples were compared against samples of treatment composition (DHN+TMPyP+Fe(III)) in anaerobic conditions under visible light irradiation to determine if m-THPP and p-THPP were effective with DHN and Fe(III) to form a treatment composition.

The preliminary data showed that m-THHP or p-THHP are also capable of producing hydroxyl radicals and Juglone or its derivatives under anaerobic conditions in the presence of DHN and Fe(III) ions in presence of visible light.

Figure 19:
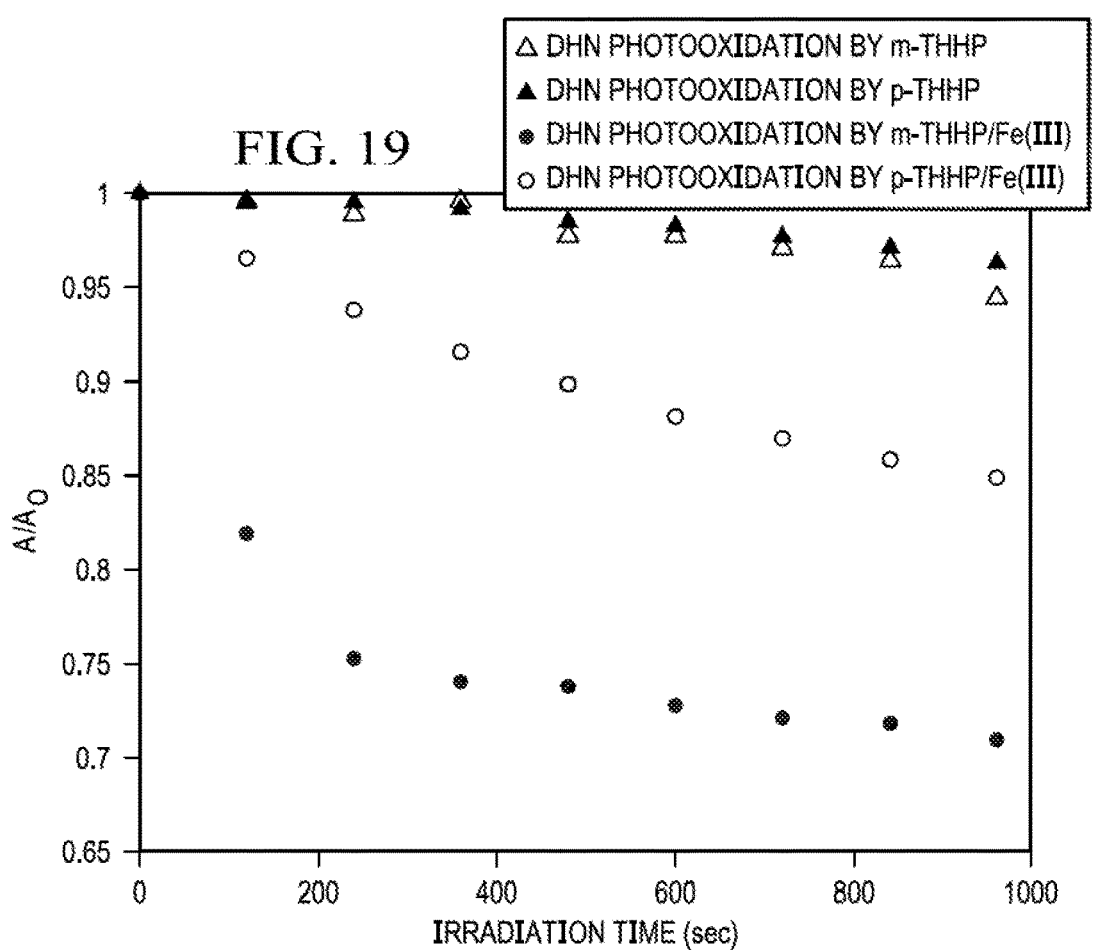
FIG. 19 shows comparisons of photooxidation of DHN by (i) m-THHP, (ii) p-THHP, (iii) m-THHP/Fe(III) or (iv) p-THHP/Fe(III) under anaerobic conditions in presence of visible light.

FIG. 19 shows comparisons of photooxidation of DHN by (i) m-THHP, (ii) p-THHP, (iii) m-THHP/Fe(III) or (iv) p-THHP/Fe(III), in acetonitrile:water (6:4), where un-shaded triangles represent for DHN photooxidation by m-THHP, shaded triangles represent for DHN photooxidation by p-THHP or shaded circles represent for DHN photooxidation by m-THHP/Fe(III), un-shaded circles represent for DHN photooxidation by p-THHP/Fe(III).

The first order rate constants of DHN photooxidation in anaerobic conditions by m-THHP/Fe(III) or p-THHP/Fe(III) were calculated and compared with rates what were observed for m-THHP or p-THHP.

Table 4 summarizes all rate constants obtained from the photooxidation of DHN by m-THHP or p-THHP or m-THHP/Fe(III) or p-THHP/Fe(III) in anaerobic conditions.

TABLE 4

| Compound | Rate (sec$^{-1}$) | R$^2$ |
|---|---|---|
| m-THP | 4.00E−05 | 0.9746 |
| m-THP w/1E−4 Fe (III) | 1.20E−03 | 0.9471 |
| p-THP | 2.00E−05 | 0.7034 |
| p-THP w/1E−4 Fe (III) | 0.0003 | 0.9957 |

As shown in FIG. 19 and Table 4, m-THHP or p-THHP are unable to produce any ROS in anaerobic conditions without Fe(III) that can cause photooxidation of DHN under anaerobic conditions. However, in the presence of Fe(III) ions, m-THHP or p-THHP are able to photooxidize DHN under anaerobic conditions.

This data teaches that (DHN+m-THHP+Fe(III)) and (DHN+p-THHP+Fe(III)) are capable as treatment compounds of producing hydroxyl radicals and Juglone or its derivatives in anaerobic conditions in presence of visible light in a manner similar to (DHN+TMPyP+Fe(III)).

Example 13

Tests were conducted, using above described materials, apparatus and methods, to evaluate generation of singlet oxygen, hydroxyl radical (ȮH) and Juglone by use of m-THPP and p-THPP with DHN and Fe(III) to determine if m-THPP and p-THPP were effective with DHN and Fe(III) in a manner similar to TMPyP in aerobic conditions under visible light irradiation.

That is, samples of formulated meso-tetra(m-hydroxyphenyl)porphine (m-THPP) combined with DHN and Fe(III) ions and samples of formulated meso-tetra(p-hydroxyphenyl)porphine (p-THPP) combined with DHN and Fe(III) were compared against samples of treatment composition (DHN+TMPyP+Fe(III)) in aerobic conditions under visible light irradiation to determine if m-THPP and p-THPP were effective with DHN and Fe(III) to form a treatment composition.

The preliminary data showed that m-THHP or p-THHP are effective to produce singlet oxygen, hydroxyl radical, and Juglone or its derivatives under aerobic conditions in presence of visible light.

Figure 20:
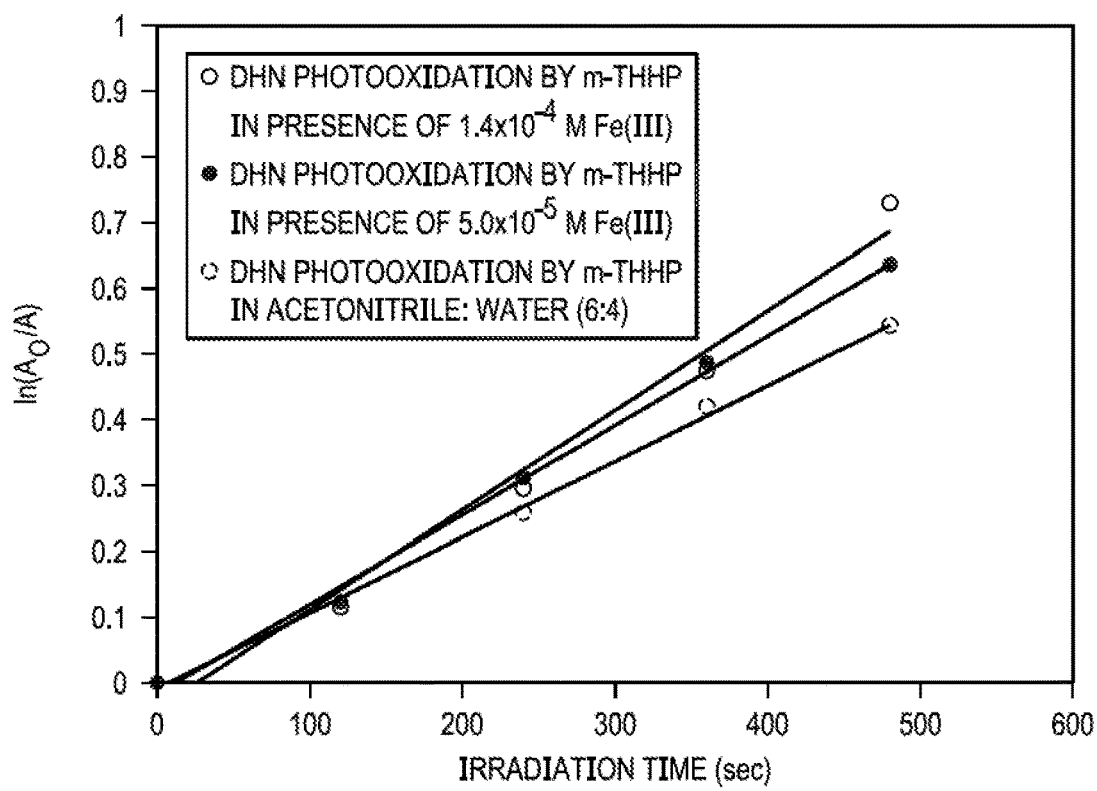
FIG. 20 shows comparisons of photooxidation of DHN by (i) m-THHP and (ii) m-THHP/Fe(III) under aerobic conditions in presence of visible light.

FIG. 20 shows comparisons of photooxidation of DHN by (i) m-THHP, (ii) p-THHP, (iii) m-THHP/Fe(III) and (iv) p-THHP/Fe(III).

The first order rate constants of DHN photooxidation in aerobic conditions by m-THHP/Fe(III) or p-THHP/Fe(III) were calculated and compared with rates what were observed for m-THHP or p-THHP.

Table 5 summarizes all rate constants obtained from the photooxidation of DHN by m-THHP or p-THHP or m-THHP+Fe(III) or p-THHP+Fe(III) in aerobic conditions.

TABLE 5

| Compound | Rate (sec$^{-1}$) | R$^2$ |
|---|---|---|
| m-THP | 0.0012 | 0.9977 |
| m-THP w/IE−4 Fe(III) | 0.0015 | 0.9831 |
| m-THP w/5E−5 Fe(III) | 0.0014 | 0.9963 |
| p-THP | 0.0008 | 0.9992 |
| p-THP w/IE−4 Fe(III) | 0.0005 | 0.9934 |
| p-THP w/5E−5 Fe(III) | 0.0007 | 0.9972 |

As shown in Table 5. DHN photooxidation by m-THHP is 1.25 times faster in the presence of 1.4×10$^{-4}$ M Fe(III) ions and 1.17 times faster in the presence of 5.0×10$^{-5}$ M Fe(III) ions, whereas comparable rates of photooxidation were observed for DHN by p-THHP in presence of Fe(III) ions. By using methods disclosed herein, optimum concentration of Fe(III) for efficient photooxidation of DHN by p-THHP can be determined.

FIG. 20 shows the photooxidation of DHN by m-THHP and m-THHP+Fe(III) where un-shaded circles represent for DHN photooxidation by m-THHP in presence of $1.4 \times 10^{-4}$ M Fe(III), shaded circles represent for DHN photooxidation by m-THHP in presence of $5.0 \times 10^{-5}$ M Fe(III), and dashed un-shaded circles represent for DHN photooxidation by m-THHP in acetonitrile:water (6:4).

Figure 21:
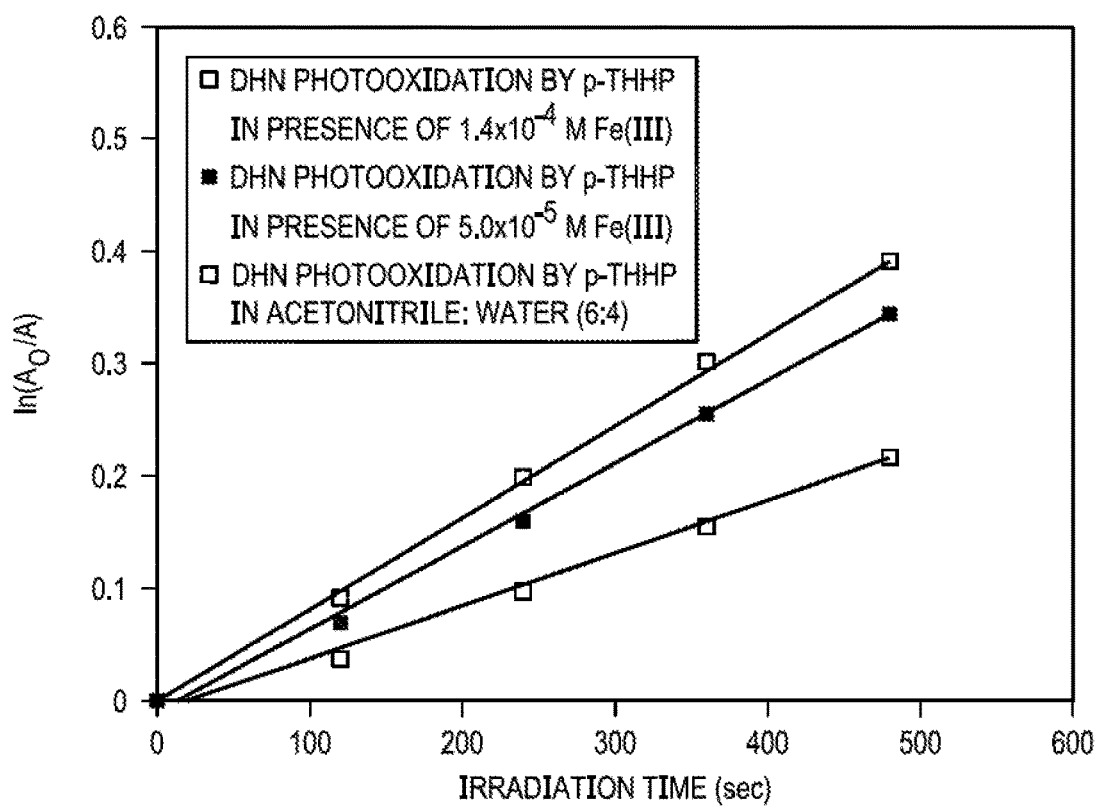
FIG. 21 also shows comparisons of photooxidation of DHN by (i) p-THHP, and (ii) p-THHP/Fe(III) under aerobic conditions in presence of visible light.

FIG. 21 shows the photooxidation of DHN by p-THHP and p-THHP/Fe(III) where un-shaded squares represent for DHN photooxidation by p-THHP in presence of $1.4 \times 10^{-4}$ M Fe(III), solid squares represent for DHN photooxidation by p-THHP in presence of $5.0 \times 10^{-5}$ M Fe(III), and dashed un-shaded squares represent for DHN photooxidation by p-THHP in acetonitrile:water (6:4).

This data, even though limited, teaches that (DHN+m-THHP+Fe(III)) and (DHN+p-THHP+Fe(III)) are capable as treatment compounds by producing singlet oxygen, hydroxyl radicals and Juglone or its derivatives in aerobic conditions in the presence of visible light in a manner similar to (DHN+TMPyP+Fe(III)).

Example 14

In vitro effects of treatment composition (DHN+TMPyP+Fe(III)) on BL21 *E. coli* in aerobic conditions under visible light irradiation were tested and are reported in FIG. 22. FIG. 22 shows *E. coli* growth, monitored after 48 hours.

To determine utility for treatment of bacteria of the claimed treatment compositions, the treatment composition was tested to see if it inhibits *E. coli* bacteria.

A "light versus dark" comparison study was performed by introducing treatment composition into two equal concentrations of *E. coli* bacteria solutions, one *E. coli* solution was kept in dark while other was irradiated with visible light.

Figure 22A:
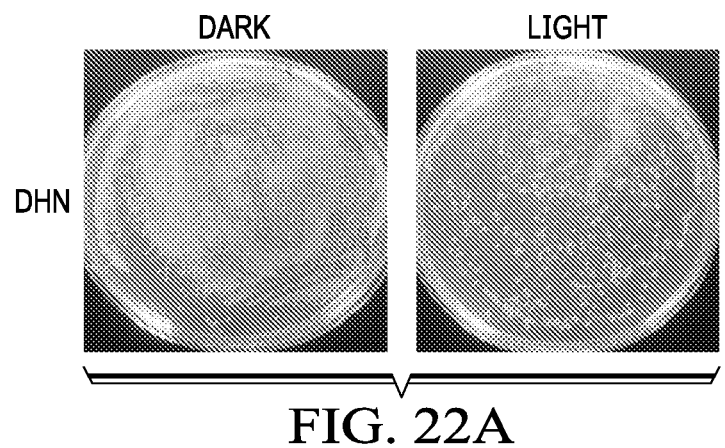
FIG. 22 compares in vitro effects on BL21 *E. coli* in aerobic conditions under visible light irradiation and at dark conditions of FIG. 22E a variation of claimed treatment composition (DHN+TMPyP+Fe(III)) against in FIG. 22A, FIG. 22B, FIG. 22C, FIG. 22D, and FIG. 22F various components of treatment composition or results when each tested alone or in combinations less than all preferred components of treatment composition.
Figure 22B:
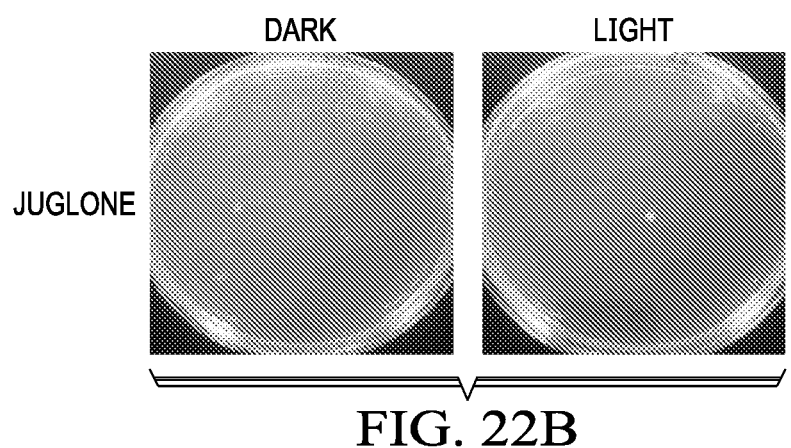
Figure 22C:
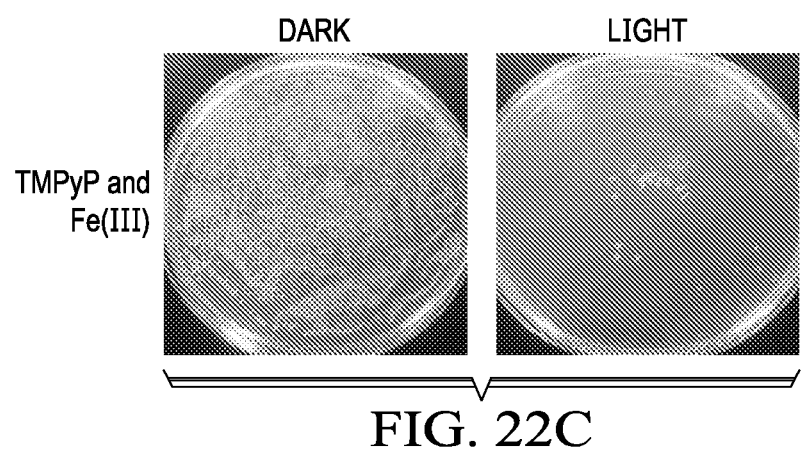
Figure 22D:
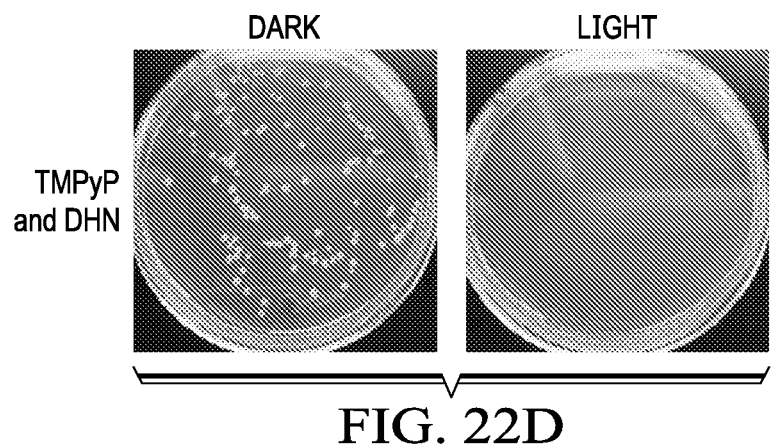
Figure 22E:
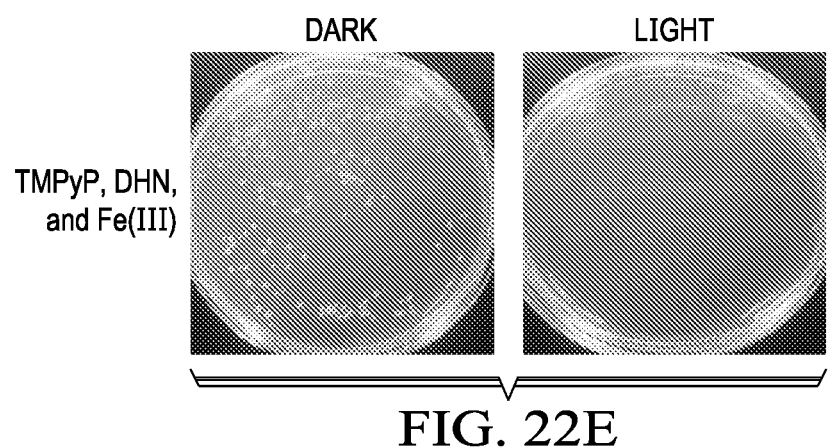
Figure 22F:
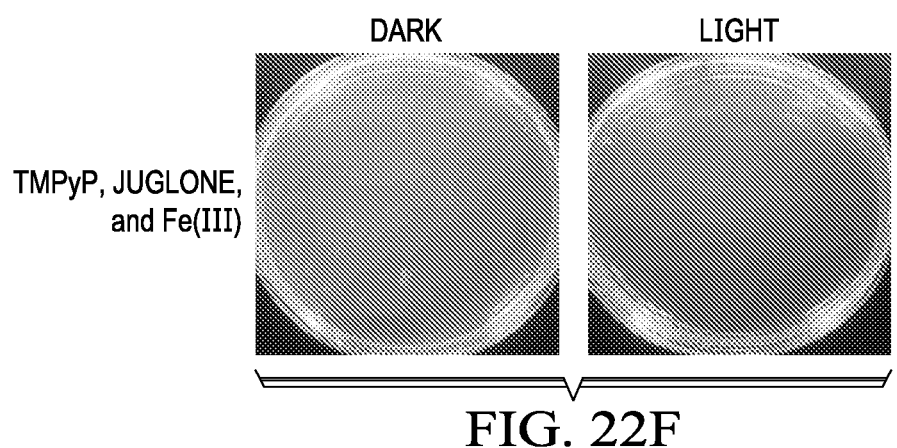

As part of the test, a comparison study, including "light versus dark" was performed of treatment composition (FIG. 22E Fe(III) ($3.5 \times 10^{-4}$ M), DHN ($4.2 \times 10^{-4}$ M) and TMPyP ($2.1 \times 10^{-5}$ M), versus FIG. 22A DHN ($4.2 \times 10^{-4}$ M), FIG. 22B Juglone ($4.2 \times 10^{-4}$ M), FIG. 22C Fe(III) ($3.5 \times 10^{-4}$ M) and TMPyP ($2.1 \times 10^{-5}$ M), FIG. 22D DHN ($4.2 \times 10^{-4}$ M) and TMPyP ($2.1 \times 10^{-5}$ M), and FIG. 22F Fe(III) ($3.5 \times 10^{-4}$ M), Juglone ($4.2 \times 10^{-4}$ M) and TMPyP ($2.1 \times 10^{-5}$ M).

The inhibition of *E. coli* growth was recorded after 48 hours and the *E. coli* growth observed for solutions kept in dark were compared with the *E. coli* growth of solutions treated with light.

As depicted in FIG. 22A, DHN alone at experimental concentration ($1.2 \times 10^{-4}$ M) showed almost no inhibition of growth of *E. coli* for dark treated sample whereas the light treated sample showed a very marginal inhibition effect of *E. coli* growth.

FIG. 22B confirms complete inhibition of growth of *E. coli* when *E. coli* solutions are treated with Juglone in dark or exposed to visible light. That is a confirmation since Juglone has been known for its antibacterial behavior for decades.

Interestingly, when TMPyP/Fe(III) ions were added to any of *E. coli* solutions and the solution was irradiated with visible light, an almost complete inhibition of *E. coli* growth was observed.

However, when TMPyP/Fe(III) ions were added to the *E. coli* solutions but the solution was kept in dark, absolutely no inhibition was observed. See FIG. 22C. This teaches that the TMPyP/Fe(III) ions produce reactive oxygen species leading to the *E. coli* inhibition.

A very similar result was obtained when TMPyP/DHN solution was reacted with *E. coli* solution under visible irradiation. See FIG. 22D. Therefore, the TMPyP solution produced an adequate amount of ROS as well as Juglone or derivatives of Juglone from DHN under visible light irradiation and the both the ROS and Juglone slowed the progression of and were detrimental to *E. coli*.

The claimed treatment composition TMPyP/DHN/Fe(III) ions produced the same results (see FIG. 22E as seen for TMPyP/DHN solution under visible light irradiation. See FIG. 22D. A total inhibition of *E. coli* was observed with the claimed treatment composition under visible light irradiation. I theorize that the claimed treatment composition forms ROS or Juglone or derivatives of Juglone which are the key species for partial or total inhibition of *E. coli* bacteria. Thus the treatment composition has properties that slow or stop the progressions of bacteria and cancers.

Example 15

In vitro effects of treatment composition DHN+TMPyP+Fe(III) on BL21 *E. coli* in in hydrogen peroxide rich environment under dark conditions were tested and are reported in FIG. 23. FIG. 23 shows *E. coli* growth, monitored after 48 hours.

Figure 6C:
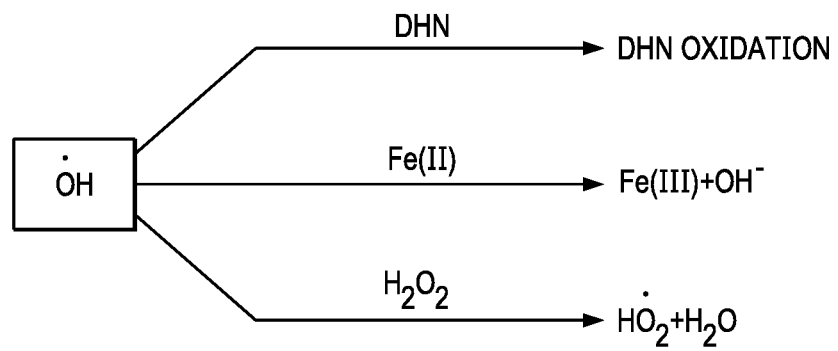

As noted in FIG. 6C showing reactions' Scheme 3, Fe(III) ions and hydrogen peroxide are common reagents in the Fenton-like reaction which produces ROS, such as HȮ, HȮ$_2$ radicals and these ROS are known for inactivation of *E. coli* bacteria.

Figure 23A:
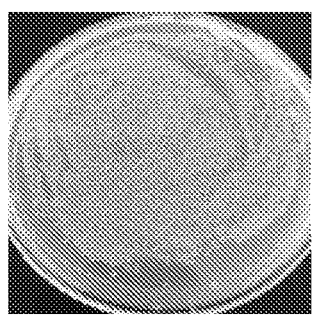
FIG. 23 shows in vitro effects on BL21 *E. coli* under dark conditions in hydrogen peroxide rich environment of a preferred variation of claimed treatment composition (DHN+TMPyP+Fe(III)) at FIG. 23E compared against various Fe(III) and/or $H_2O_2$ concentrations in FIG. 23A, FIG. 23B, FIG. 23C, and FIG. 23D.
Figure 23B:
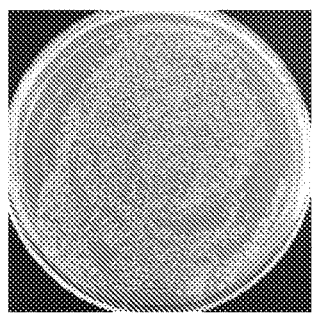
Figure 23C:
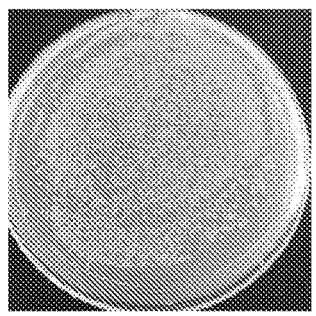
Figure 23D:
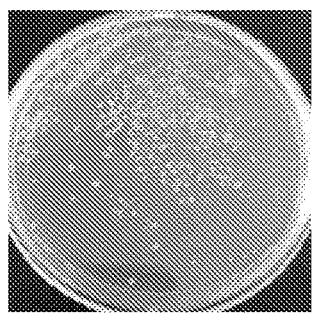
Figure 23E:
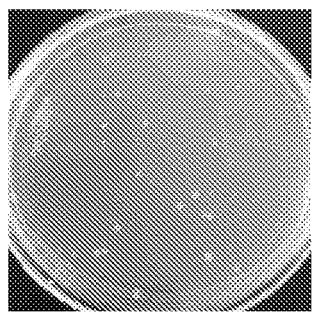

To determine utility for treatment of bacteria of the claimed treatment compositions in an aqueous $H_2O_2$ rich environment (typical tumor environment), *E. coli* bacteria were mixed with the treatment composition in the presence of $H_2O_2$ in dark conditions under normal room temperature and pressure. As shown in FIG. 23E, a substantial inhibition of growth of *E. coli* was observed when $1.0 \times 10^{-4}$ M Fe(III) ions and 400 μM $H_2O_2$ were used to react with *E. coli* bacteria. A series of control reactions were carried out to see if alone, any of Fe(III) ions with $1.0 \times 10^{-4}$ M concentration (FIG. 23A) or Fe(III) ions with $1.0 \times 10^{-3}$ M concentration (FIG. 23B) or 400 μM $H_2O_2$ (FIG. 23C) can inhibit the growth of *E. coli* bacteria under identical reaction conditions. No noticeable inhibition of growth of *E. coli* bacteria was observed when Fe(III) ions or $H_2O_2$ at the experimental concentration was used against *E. coli*. After 48 hours, an almost complete inhibition of *E. coli* was observed (FIG. 23E) when ten times concentrated Fe(III) ions and $H_2O_2$ reacted with *E. coli* bacteria versus less quantity (FIG. 23D) teaching that at such Fe(III) concentration, the treatment composition is very effective in producing ROS for killing *E. coli* bacteria. Therefore, the claimed treatment composition is capable of producing ROS in $H_2O_2$ environment and has the full potential to be effective in tumor environment where an augmented amount of $H_2O_2$ is present.

While the above invention has been described with reference to specific embodiments of treatment compositions and methods of making and use to impair or terminate bacteria or malignant tumors, this invention can also be applied to treat other tissues and pathologies or issues such as Alzheimer's symptoms. It should be understood that the foregoing disclosure is illustrative and not limiting, and that obvious modifications may be made by those skilled in the art without departing from the spirit of this invention.

The invention claimed is:

1. A treatment or diagnosis composition comprising:
   (a) a complex comprising:
      (1) a free base tetrakis aryl (Ar) substituted porphyrine core wherein each of four Ar substituents are at meso positions, are the same, and are selected from an Ar group consisting of any of ortho-, meta-, or para-hydroxyphenyl and alkyl pyridyl,
      (2) a dihydroxynaphthalene or a hydroxynaphthalene, and
      (3) a hydrated metal having a +3 ionic state with spatial attributes at or near that occupied by Fe(III), and
   (b) comprising TMPyP (meso-tetra(N-methyl-4-pyridyl) porphine tetrachloride), 1,5-DHN (1,5-dihydroxynaphthalene) and hydrated Fe(III) in molar ratios of (i) TMPyP to 1,5-DHN of 1:18-22, (ii) TMPyP to Fe(III) ions of 1:15-18.33, and (iii) 1,5-DHN to Fe(III) ions of 1.1:1.3.

2. The composition in accordance with claim 1 which has multifunctional activity for treatment or diagnosis in the absence of or in the presence of light, or both, or under aerobic or anaerobic conditions, as determined by molar ratios of 1.(a)(1), 1.(a)(2) and 1.(a)(3).

3. The composition in accordance with claim 1, wherein the composition comprises one or more chemotherapeutic therapies selected from the group consisting of a singlet oxygen, a hydroxyl radical, and a Juglone, and wherein the composition comprises a molecular entity resulting from a loose association involving two or more component molecular entities from a combination of the 1(a)(1) porphyrine core, the 1(a)(2) naphthalene based component, and the 1(a)(3) hydrated+3 metal, wherein the hydrated+3 metal is not covalently bonded at the porphyrine core, either alone or with components present in a mammalian tissue or fluid.

4. The composition in accordance with claim 1, wherein 1.(a)(1) is selected from one or more of the group consisting of meso-tetrakis(N-methyl-4-pyridyl) porphine tetrachloride, meso-tetrakis(o-hydroxyphenyl)porphine, meso-tetrakis(m-hydroxyphenyl)porphine, and meso-tetrakis(p-hydroxyphenyl)porphine; 1.(a)(2) comprises dihydroxynaphthalene, and 1.(a)(3) comprises Fe(III) chloride; and the treatment comprises a hydroxyl radical.

5. The composition in accordance with claim 1, comprising an aqueous solution wherein 1.(a)(1) is selected from one or more of the group consisting of meso-tetrakis(N-methyl-4-pyridyl) porphine tetrachloride, meso-tetrakis(o-hydroxypheny l)porphine, meso-tetrakis(m-hydroxyphenyl)porphine, and meso-tetrakis(p-hydroxyphenyl) porphine; 1.(a)(2) comprises dihydroxynaphthalene, and 1.(a)(3) comprises Fe(III) chloride; and the treatment composition comprises one or more of a hydroxyl radical, a singlet oxygen, and a Juglone; and a molar ratio of 1.(a)(3) Fe(III) chloride is increased or decreased in relation to 1.(a)(1) or 1.(a)(2) dihydronapthalene.

* * * * *